United States Patent
Olwin et al.

(10) Patent No.: US 8,992,906 B2
(45) Date of Patent: Mar. 31, 2015

(54) COMPOSITIONS AND METHODS FOR ENGRAFTMENT AND INCREASING SURVIVAL OF ADULT MUSCLE STEM CELLS

(75) Inventors: Bradley Bruce Olwin, Boulder, CO (US); John K. Hall, Boulder, CO (US); Kathleen Kelly Tanaka, Parker, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 760 days.

(21) Appl. No.: 12/595,595

(22) PCT Filed: Apr. 11, 2008

(86) PCT No.: PCT/US2008/060017
§ 371 (c)(1),
(2), (4) Date: Mar. 19, 2010

(87) PCT Pub. No.: WO2008/128031
PCT Pub. Date: Oct. 23, 2008

(65) Prior Publication Data
US 2010/0226898 A1  Sep. 9, 2010

Related U.S. Application Data

(60) Provisional application No. 60/911,350, filed on Apr. 12, 2007.

(51) Int. Cl.
| | | |
|---|---|---|
| A61K 35/12 | (2006.01) | |
| A61K 35/34 | (2006.01) | |
| A61K 38/00 | (2006.01) | |
| C12N 5/00 | (2006.01) | |
| C12N 5/06 | (2006.01) | |
| C12N 5/077 | (2010.01) | |

(52) U.S. Cl.
CPC ............... *C12N 5/0659* (2013.01); *A61K 35/12* (2013.01)
USPC .......... 424/93.1; 424/93.7; 435/325; 435/366; 435/384; 530/300

(58) Field of Classification Search
USPC ................ 424/93.1, 93.7; 435/325, 366, 384; 530/300
See application file for complete search history.

(56) References Cited

U.S. PATENT DOCUMENTS 6,800,286 B1 * 10/2004 Olwin et al. ............... 424/185.1

OTHER PUBLICATIONS

Meeson et al, Stem Cells 22:1305-1320, 2004.*
Asakura et al, J. Cell Biology 159(1):123-134, 2002.*
Cornelison et al, Dev. Biol. 239:79-94, 2001.*
Asakura et al, Trends Cardiovasc. Med 13:123-128, 2003.*
Doyle et al., "Abcg2 labels multiple cell types in skeletal muscle and participates in muscle regeneration", J. Cell Biol. 2011; 195(1):147-163.
Troy et al., "Coordination of Satellite Cell Activation and Self-Renewal by Par-Complex-Dependent Asymmetric Activation of p38alpha/beta MAPK", Cell Stem Cell 2012; 11: 541-553.
Tanaka et al., "Syndecan-4-Expressing Muscle Progenitor Cells in the SP Engraft as Satellite Cells during Muscle Regeneration", Cell Stem Cell 2009; 4: 217-225.

* cited by examiner

*Primary Examiner* — Kevin Hill
(74) *Attorney, Agent, or Firm* — Faegre Baker Daniels LLP

(57) ABSTRACT

Embodiments herein relate to compositions and methods for engraftment of and increasing survival of muscle cells in a subject in need thereof. In certain embodiments, compositions including myofibers and/or satellite stem cells may be administered to a subject. Other embodiments relate to compositions and methods for introducing one or more compounds to a subject using cell compositions disclosed herein. Still other embodiments relate to uses of these compositions in kits for portable applications and methods.

29 Claims, 14 Drawing Sheets

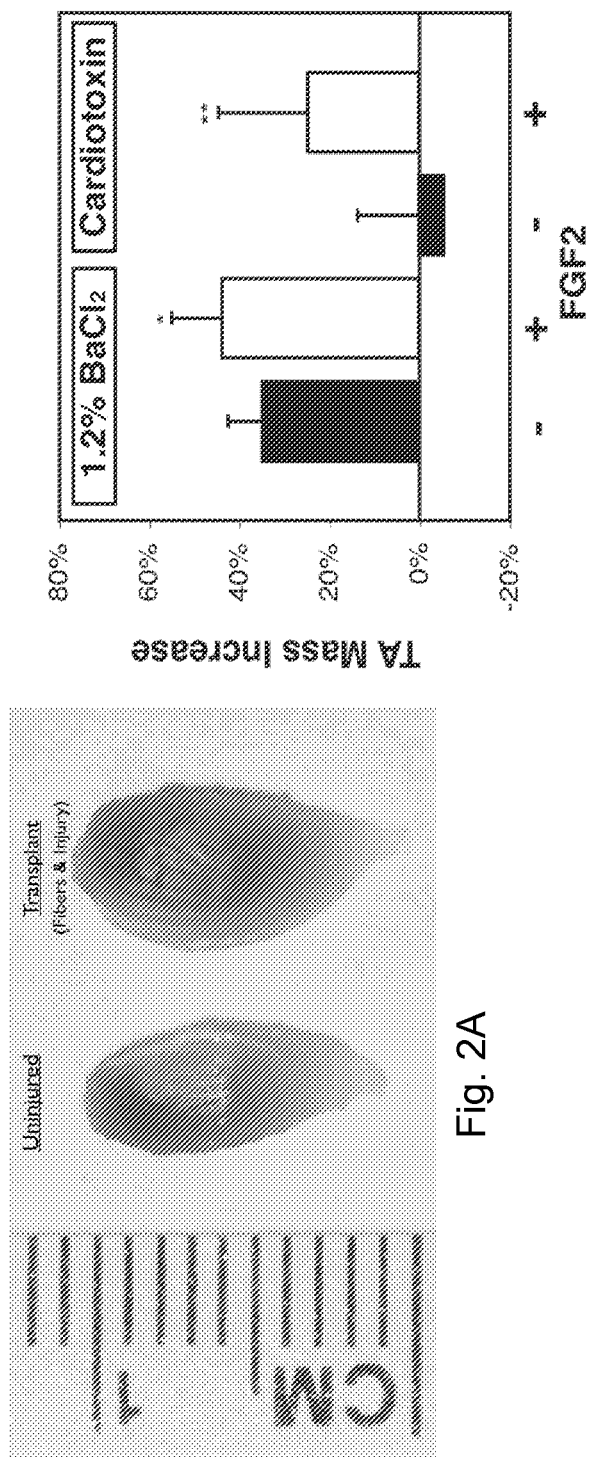

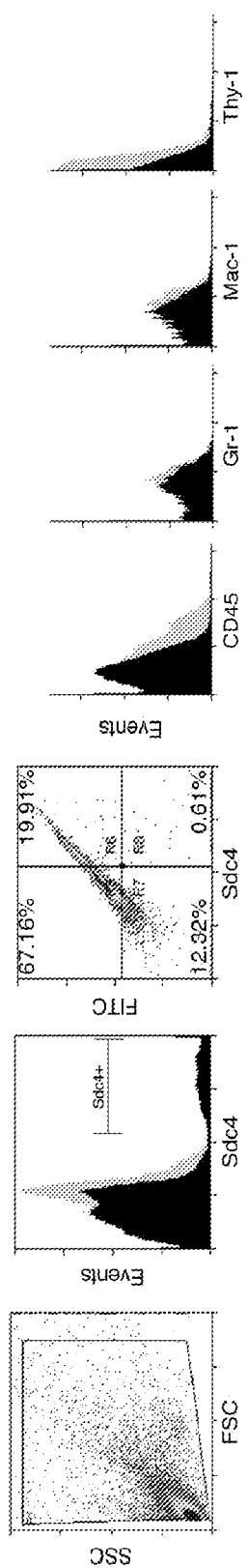
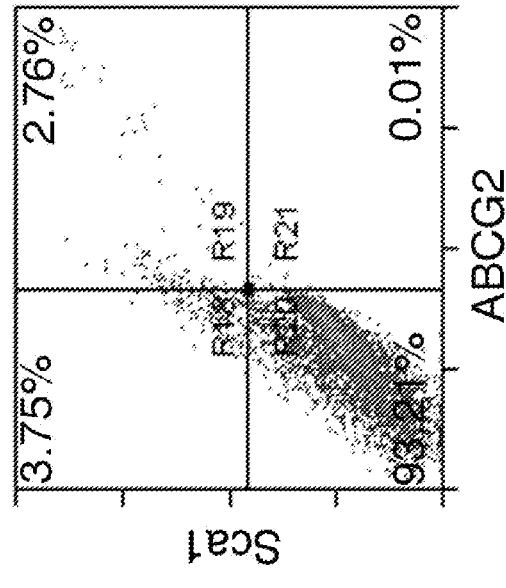
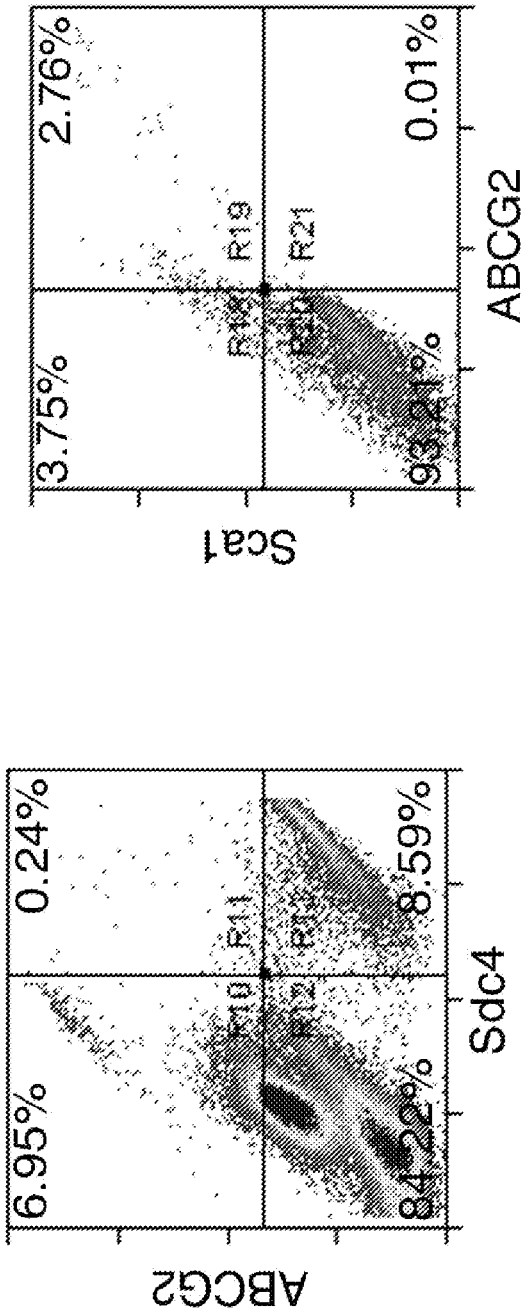
Fig. 9A
Fig. 9B
Fig. 9C

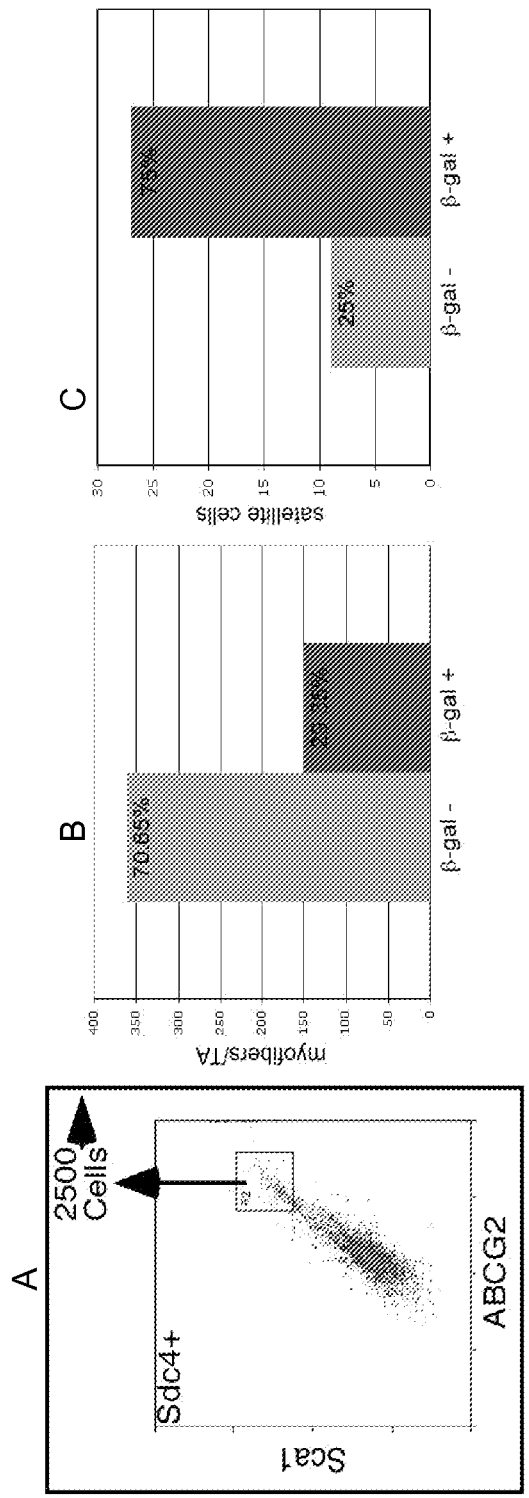
Figs. 10A-C

COMPOSITIONS AND METHODS FOR ENGRAFTMENT AND INCREASING SURVIVAL OF ADULT MUSCLE STEM CELLS

PRIORITY

This application claims the benefit under 35 USC §119(e) of provisional U.S. patent application Ser. No. 60/911,350 filed on Apr. 12, 2007, which is incorporated herein by reference in its entirety.

GOVERNMENT FUNDING

This invention was made with government support under grant numbers AR049446 and AR039467 awarded by the National Institutes of Health. The government has certain rights in the invention.

FIELD

Embodiments herein relate to compositions and methods for engraftment of and increasing survival of adult muscle stem cells. Other embodiments relate to compositions and methods for introducing one or more compound to a subject using stem cell compositions disclosed herein. Still other embodiments relate to uses of these compositions in kits for portable applications and methods.

BACKGROUND

Maintenance and repair of skeletal muscle tissue is essential for survival of locomotor organisms. For example, muscle strains or tears can happen when a muscle is stretched beyond its limit or if there is a direct blow to a muscle, tearing the muscle fibers. Muscle injury frequently occurs near the point where the muscle joins the tough, fibrous connective tissue of the tendon. Muscle injuries are common and range from where only a few muscle fibers are stretched or torn, to more severe tears with muscle pain and tenderness, mild swelling, noticeable loss of strength and sometimes bruising, to muscle tears that rip the muscle into two separate pieces or cause the fleshy part of the muscle to break away from the tendon, resulting in complete loss of muscle function, considerable pain, swelling, tenderness and discoloration.

During aging, much of the muscle mass is lost. In addition, fiber-type changes occur and increased fat deposition in muscle occurs. Loss of mass and these other changes can have a significant impact on the ability of an individual to continue to perform certain daily activities, as well as participate in more strenuous activities, possible earlier in life.

In addition to regular maintenance and repair of muscle tissue that is associated with normal activities in most individuals, there are also significant diseases that affect the muscle tissue. The muscular dystrophies are a group of muscle diseases which have three features in common including hereditary; progressive; and cause a characteristic, selective pattern of weakness, in particular, progressive skeletal muscle weakness, defects in muscle proteins, and the death of muscle cells and tissue (e.g., see Emery A E (2002)).

Dystrophin-associated muscular dystrophies range from the severe Duchenne muscular dystrophy (DMD), which is the most common muscular dystrophy, to the milder Becker muscular dystrophy (BMD). Mapping and molecular genetic studies indicate that both are the result of mutations in the huge gene that encodes dystrophin. Duchenne muscular dystrophy eventually affects all voluntary muscles, as well as heart and breathing muscles. Survival is rare beyond the early 30 s, and death typically occurs from respiratory failure (suffocation) or heart disorders.

Satellite cells, which lie juxtaposed to the myofiber and underneath the basal lamina, are a source of new myonuclei required for skeletal muscle growth, repair and regeneration (see for example Mauro, 1961; Schultz and McCormick, 1994). In uninjured skeletal muscle, the majority of these cells are mitotically quiescent, exhibit a high nuclear to cytoplasmic volume and do not express members of the MyoD family of transcription factors (Cornelison and Wold, 1997; Schultz et al., 1978). Once activated, these cells rapidly increase their cytoplasmic volume, egress from the basal lamina and proliferate prior to their fusion into existing, damaged myofibers or with each other to form new myofibers (see for example Hawke and Garry, 2001; and Smith et al., 1994). Most satellite cells divide only once or twice prior to fusion and a subpopulation of satellite cells fail to fuse and fail to incorporate DNA label over 14 days, suggesting they comprise a quiescent "reserve" cell pool.

Accordingly, there remains a need for improved methods and compositions for the engraftment and/or repair of muscle tissue, including injured, aged and diseased muscle tissue.

SUMMARY

Embodiments herein concern methods and compositions for the engraftment and/or repair of muscle tissue. Certain embodiments include, compositions including but not limited to, satellite stem cells, optionally, a media; and a modified fibroblast growth factor (FGF), wherein the modification increases cellular entry of the growth factor. In accordance with these methods, compositions can include 250 satellite stem cells or more. In certain embodiments, compositions can include an FGF-penetratin. FGF can be full-length FGF, a biologically active fragment thereof, a chimeric protein, fusion protein or a combination thereof. Certain compositions may include chimeric fibroblast growth factor (FGF) protein having (a) fibroblast growth factor biological activity that occurs in the absence of heparan sulfate; and, (b) an ability to enter a living cell in the absence of a receptor that binds to FGF. In some embodiments, satellite stem cells are obtained by harvesting the cells from one or more donors. In other embodiments, compositions include media containing serum in an amount ranging from about 1% to about 20% serum.

Some compositions contemplated herein include satellite stem cells exposed to media for about 24 hours or less. In accordance with embodiments disclosed herein, satellite stem cells can include, but are not limited to, one or more of Syndecan-4 positive; ABCG2 positive; form myotubes if cultured in vitro; engraft into the satellite cell niche in vivo; self-renewing or combination thereof. Certain satellite stem cell compositions may be Sca1. Other satellite stem cell compositions may be Pax7.

Other compositions may include composition for delivering compounds to a subject including satellite stem cells having or capable of producing one or more compound(s) associated with one or more of the cells; and modified FGF, wherein the modification increases cellular entry of the growth factor. In accordance with these embodiments, a compound may include, but is not limited to one or more of a gene, a protein, a peptide, a nucleic acid sequence, an ion, a chemical or a combination thereof. In certain compositions, one or more compounds for delivery may include but are not limited to lipoproteins, clotting factors, clotting enzymes, other growth factors, or combinations thereof. Certain compounds may include Insulin, or clotting factor IX. In general, compositions could be made to deliver cell-produced biologically active molecules into the bloodstream.

Other compositions contemplated herein include, but are not limited to, satellite stem cells; one or more growth factors; and one or more carbohydrate compositions. In accordance with these embodiments carbohydrate composition may include a heparan sulfate composition. In addition, other characteristics regarding satellite stem cells disclosed herein may also be characteristics of compositions having one or more carbohydrate compositions.

Other embodiments herein concern methods for providing one or more of supplement and replenishment for a muscle cell population in a subject including, but not limited to, obtaining a satellite stem cell population capable of one or more of supplement and replenishment of muscle cell populations; incubating the population with a media for 24 hours or less; providing a growth factor and/or modified fibroblast growth factor (FGF) to the population, wherein the modification increases cellular entry of the FGF; and administering the population to muscle tissue of the subject in need thereof. In some embodiments, growth factors may include, but are not limited to HGF (hepatocyte growth factor), TNFalpha (tumor necrosis factor alpha), CCL4 (Chemokine (C—C motif) ligand 4) or combinations thereof. Certain methods and compositions contemplated herein can include, but are not limited to, satellite cells are from the subject or in other embodiments the satellite cells are from a donor. In accordance with these embodiments, the donor may be an allogeneic donor, and/or a xenogeneic donor.

Some methods contemplated herein may include injuring myofibers at a site of muscle transplant in the subject or selecting a site of muscle transplant in a subject that is injured and/or undergoing regeneration. Some subjects contemplated herein can include a human or other mammalian subject. Subjects contemplated in need of disclosed methods herein may include a subject having muscle injury, aging muscle tissue, a muscle disorder or a neurological disorder that causes muscle loss. In some methods, the satellite stem cell population may incubate in media for 24 hours or less; 18 hours or less; 12 hours or less; or 6 hours or less. In accordance with these embodiments, FGF can be a full-length FGF, a biologically active fragment thereof, an analog of, a peptide thereof, a mimetic thereof, a chimeric protein or fusion protein.

In certain embodiments, muscle tissue of the subject may be injured prior to administration of the population to the muscle tissue of the subject. Some embodiments, herein concern injuring the muscle tissue including exposing the muscle tissue to a $BaCl_2$ composition. Subjects contemplated herein include human subjects as well as other mammalian subjects including, but not limited to domesticated animals and zoo animals. In accordance with these embodiments, administering compositions contemplated herein include, but are not limited to intravenous injection, intra-arterial injection, subcutaneous injection, intramuscular injection or combinations thereof. In certain embodiments, one or more cells of the population have been genetically modified. In some embodiments, administration of compositions contemplated herein may include one administration or more administrations depending on need of the subject.

In certain embodiments, methods herein provide for delivering one or more compound(s) to a subject in need thereof include, but are not limited to, obtaining a satellite stem cell population having or capable of producing one or more compound(s) associated with one or more of the cells; incubating the population with a media for 24 hours or less; providing modified fibroblast growth factor (FGF) to the population, wherein the modification increases cellular entry of the growth factor; and administering the population to muscle tissue of the subject. wherein one or more of the cells are genetically modified. In some embodiments, muscle tissue may be injured prior to introduction of the population to the subject. In some embodiments, compositions administered to a subject can include implanting one or more donor myofiber (s) to the subject. One or more cells of the population may be genetically modified to express a growth factor. In some embodiments, one or more cells of the population have been genetically modified to express a retrovirus comprising a gene for delivery to muscle tissue and an adjacent cell or tissue. In accordance with these embodiments, one or more cells of the population have been genetically modified to express a heterologous protein or to overexpress a myocyte protein. Compositions herein can provide for one or more of muscle cell supplement and replenishment; and one or more compound(s) to the subject.

Other embodiments herein concern kits including, but not limited to, at least one container; a satellite stem cell population; a media; and one or more factors. Certain kits include factors such as growth factors where at least one growth factor is modified fibroblast growth factor (FGF), wherein the modification increases cellular entry of the growth factor.

BRIEF DESCRIPTION OF THE DRAWINGS

The following drawings form part of the instant specification and are included to further demonstrate certain aspects of particular embodiments herein. The embodiments may be better understood by reference to one or more of these drawings in combination with the detailed description presented herein.

FIG. 2A represents an exemplary digital image illustrating a contralateral tibialis anterior comparison of uninjured and injured transplanted muscle fibers 60 days post-transplantation.

FIG. 2B represents an exemplary histogram illustrating relative mass increase with and without FGF2 occurring with two distinct methods of injury.

FIG. 9A represent exemplary flow cytometry diagrams illustrating Syndecan-4 cells are about 20% of muscle cells and are not derived from blood cells.

FIG. 9B represents an exemplary flow cytomotery diagram illustrating a minor population of Syndecan-4 muscle cells express ABCG2.

FIG. 9C represents an exemplary flow cytometry diagram illustrating muscle stem cells express Syndecan-4, ABCG2 and Sca1.

FIGS. 10A-10C illustrate an example of purified muscle stem cells (A) engraft into host myofibers (B) and reside as satellite cells in host muscle (C).

DESCRIPTION OF ILLUSTRATIVE EMBODIMENTS

Definitions

Figure 1:
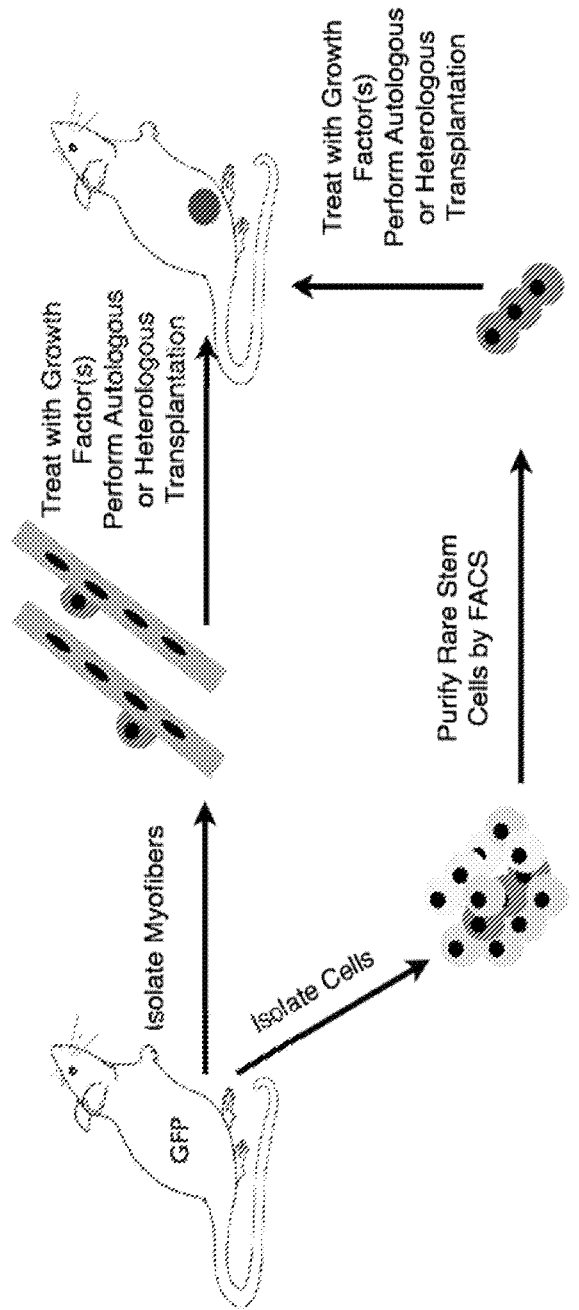
FIG. 1 represents an exemplary schematic drawing illustrating a basic protocol for muscle fiber transplantation and cell transplantation using purified muscle stem cells.

Terms that are not otherwise defined herein are used in accordance with their plain and ordinary meaning.

As used herein, "a" or "an" may mean one or more than one of an item.

As used herein, "about" can mean plus or minus 10%, for example, about 10 minutes can mean from 9 to 11 minutes.

Description

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description.

Embodiments herein generally relate to novel and efficient methods to produce and transplant muscle stem cells and muscle satellite cells for repair, supplementation and regeneration/generation of muscle tissue. Other embodiments relate to populations of satellite cells contemplated herein to be the self-renewing stem cell populations for a satellite cell population.

Long-term engraftment or repair of injured or diseased muscle tissue is of interest, which has included the exploration of stem cell therapy. However, isolation of muscle stem cells and engraftment into uninjured, injured or diseased muscle tissue has previously resulted in poor engraftment; loss of much of the stem cell population; and little or no repair of diseased or reduced muscle tissue. In one example, when stem cells are engrafted with their corresponding muscle fibers, engraftment occurs, but with frequencies that are only slightly improved upon engraftment of isolated stem cells (Skuk 2006).

Previous Studies

Discovery that cells from the bone marrow (see for example Bittner et al., 1999; Brazelton et al., 2003), the blood vessel wall (Sampaolesi et al., 2003) and from adult muscle side population (SP) (Muskiewicz et al., 2005) can participate in muscle regeneration questioned whether satellite cells are adult muscle stem cells or committed progenitor cells. This controversy remains unresolved, as a subset of satellite cells appears to possess stem cell characteristics that include asymmetric distribution of Pax7 (see for example Olguin and Olwin, 2004) during cell division. Additionally, long-term BrdU retention and nonrandom DNA segregation has been observed in satellite cell subpopulations (Shinin et al., 2006). Although these properties are consistent with those that identify other adult stem cells, the functional consequences of these events for muscle regeneration and in satellite cell self-renewal is lacking.

Various investigators have made some progress in the area of muscle cell transplantation. For example, mesoangioblasts have been transplanted into dystrophic dogs and obtained an extensive reconstitution of fibers expressing dystrophin, an improvement in the contraction force and, in many cases, a preservation of walking ability (Sampaolesi et al., 2006, Nature Online Publication). The cells were delivered by five intraarterial injections of $5 \times 10^7$ cells each (one injection per month), with concomitant immune suppression of the subjects. However, the extent of stem cell regeneration and the longevity of the treatment were unclear. Moreover, the immunosuppression of the animals is an undesirable side treatment of this procedure.

Other studies have explored genetic modification and transplantation of undeveloped muscle cells, called myoblasts, to a patient's muscle tissue. (see, for example Skuk et al., 2007; Skuk et al., 2006; Skuk and Tremblay, 2000). In one study, experiments involved the administration of human satellite cells grown to large numbers ex vivo and then transplanted in large numbers into the recipient. However, this method has been fairly inefficient, achieving no observable clinical benefit as measured by changes in force transduction of the transplanted muscles.

Other studies involved muscle-derived stem cells displaying myogenic and stem cell markers were transplanted into mice, and showed that these cells could contribute to a persistent restoration of dystrophin myofibers within the transplanted muscle, in which a large number of small regenerating myofibers could be observed for up to 90 days after injection. The cells were transplanted (single-point injection) in the gastrocnemius muscle of mdx mice (C57BL/10ScSn DMDmdx/J). The mdx mice used as recipients in this experiment were not immunosuppressed, and the injected muscles were not preirradiated or injured with a myonecrotic agent before transplantation. However, results from animal and human clinical trials have suggested that although myoblast transplantation is feasible, it is rather inefficient. The low survival rate, poor spreading of transplanted cells, and immunorejection of the donor cells are still major problems facing myoblast transplantation.

Transplantation of Stem Cells

Some embodiments herein relate to development of a procedure for transplantation of skeletal muscle stem cells and skeletal muscle satellite cells, enabling high efficiency engraftment of cells into the muscle tissue (defined herein as myofibers), as well as the satellite cell niche. Serial transplantation experiments demonstrated that a population of self-renewing stem cells can be engrafted that is expected to populate the tissue indefinitely. Other methods herein have demonstrated that a population of satellite cells can be isolated that exhibit stem cell behavior and engrafts exclusively into the satellite cell niche and does not engraft as nuclei into the existing myofiber, indicating that this population can be a self-renewing stem cell for the satellite cell population. This cell has not been previously described.

Methods for transplantation are described herein. In certain embodiments engraftment can be robust, with over 50% of the endogenous myofibers receiving engrafted cells. Unexpectedly, a majority of stem cells present in the engrafted muscle tissue are of donor origin, not host origin, and exceed the host stem cells by about 5-fold to about 10-fold. In certain embodiments, transplanted or engrafted muscle can be increased by approximately 50% in dry and wet weight. In accordance with these embodiments, compositions disclosed herein have extensive potential for repair of minor to severe muscle injury and for treatment of muscular diseases, such as muscular dystrophies, among other muscle repair and maintenance protocols.

In certain embodiments, compositions for engraftment may be maintained in contact with their native environment or niche. Therefore, procedures herein can include isolated myofibers in addition to their associated satellite cells and satellite stem cells. Other embodiments herein may include compositions that include satellite stem cells. In certain embodiments, one or more myofiber may have between 15 and 20 associated satellite cells. Other compositions, contemplated for engraftment may be exposed to a media having one or more growth factors. For example, certain satellite stem cell populations and/or isolated myofibers can include fibroblast growth factor (FGF). Incubation periods with media compositions may include a period of 24 hours or less; 18 hours or less; 12 hours or less or 6 hours or less.

In some embodiments, satellite stem cell compositions may be administered alone, or after incubation with media compositions disclosed herein. In certain embodiments, media compositions include growth factors. In certain embodiments, satellite stem cell compositions and/or myofibers can be exposed to a media having a growth factor containing FGF and then the compositions engrafted into the muscle of a subject, as observed in the results of implantation techniques previously described. In certain embodiments, compositions exposed to media including FGF or a modified form of FGF can increase muscle mass in a site of engraftment or within a muscle tissue on the order of 30-50%, 40-60%, 50%-70%, 60-80% or 80-100%. In other embodiments, media compositions can include FGF, HGF (hepatocyte growth factor), TNFalpha (tumor necrosis factor alpha), CCL4 (Chemokine (C—C motif) ligand 4), other physiological factors, other growth factors or combinations thereof.

Methods herein are highly efficient muscle cell engraftment compositions and methods. In certain embodiments, satellite stem cell compositions administered to a subject in need thereof may include a single administration. For example, transplantation of a single myofiber works under certain circumstances as well as transplantation of 20 myofibers in examples herein. Some embodiments herein, include high level of donor cell engraftment, including engraftment of self-renewing muscle satellite cells, and grafts persist long term with reduced loss of muscle mass. In other embodiments, compositions and methods herein elicit reduced to undetectable anti-graft immune response. Thus, immunosuppression of the subject may not be needed. Moreover, the transplanted myofibers may be implanted within about 6 hours or less from the time of isolation, and so the method is not only very rapid to perform, but also avoids issues related to culture of cells or tissue (e.g., avoids problems with contamination or undesired cell growth, expansion, or modulation of phenotype).

Other embodiments concern methods for using compositions disclosed herein for introducing exogenous genes into the transplanted muscle cells, for example, to correct or complement any genetic defect in muscle cells or even another tissue. Identification, isolation and characterization of self-renewing, long term repopulating satellite cells described herein, provide for methods readily expanded to include transplantation of these cells, alone or in conjunction with myofibers. Further, genetic modification of satellite cells for administration alone, or in conjunction with myofibers, is also contemplated.

Accordingly, some embodiments relate to methods to maintain or repair muscle tissue, using methods disclosed herein for muscle cell transplantation. In accordance with these embodiments, one method can include: providing satellite stem cell compositions or myofiber compositions to a subject in need thereof. In some embodiments, cellular compositions may be isolated from a donor, wherein the cells include muscle cells, including satellite cells, from a donor. In other methods, satellite stem cell compositions or myofiber compositions can be incubated in a medium including, but not limited to, fibroblast growth factor media compositions. In certain more particular embodiments, subjects may be injured at the site of muscle transplant prior to administration of compositions herein.

As used herein, a "myofiber" can be defined as commonly understood in the art, and refers to a multinucleated, single muscle cell. As used herein, a "satellite" cell can be defined as commonly understood in the art and refers to mononucleated, myogenic cells, located between the sarcolemma and basement membrane of terminally-differentiated myofibers. Satellite cells are normally quiescent in adult muscle, but act as a reserve population of cells, able to proliferate in response to injury and give rise to regenerated muscle and to more satellite cells.

Methods disclosed herein demonstrate that as few as one myofiber can be transplanted into a host (recipient) and successfully implant and increase the muscle mass at the site of transplant. In fact, the inventors have demonstrated that transplantation of a single myofiber can be as effective as transplantation of 5, 10 or 20 myofibers. Accordingly, the provision of at least one myofiber for transplantation refers to the provision of one or more myofibers for transplantation at a single site in a host recipient, and can include the provision of 2, 3, 4, 5, 6, 7, 8, 9, 10, 11, 12, 13, 14, 15, 16, 17, 18, 19, 20, or more myofibers for transplantation at a single site in a host recipient, including any additional number of fibers, in whole number increments (e.g., 21, 22, 23 . . . ), up to 15, 50, 75, 100, or more myofibers for transplantation at a single site in a host recipient. In other embodiments, administering satellite stem cells to a subject may include administering, as few as one stem cell, to administering 1-10; 10-50; 50-200; 200-500; 500-1,000; 1000-1,500; 1,500-2,000 or more satellite stem cells to a subject in need thereof.

In some embodiments, satellite stem cells and/or myofibers can be provided by obtaining the fibers from any suitable donor, including from autologous tissue, from an allogeneic donor and from a xenogenic donor. In certain embodiments, the donor is the same as the host (e.g., the fibers can be autologous to the individual receiving the transplant, but obtained from a different location or site in the body of the individual). In one embodiment, the donor can be from the same species as the host, but is a different individual than the host (an allogeneic donor). In another embodiment, the donor is from a different species than the host (a xenogeneic donor). An allogenic donor is preferably tissue-matched to the recipient (selected for immunocompatibility), to account for major and minor histocompatibility antigens and provide the greatest chance of graft acceptance. However, providing satellite stem cells and/or myofibers from any suitable source, including unmatched donors and xenogeneic donors (e.g., porcine into human) is contemplated herein. Immunosuppression may be used on the host to ensure graft acceptance, if needed under the circumstances presented. Thus, compositions disclosed herein may be combined with administration of immunosuppressive agents to a subject in need thereof.

Methods for obtaining myofibers from a variety of mammals has been described. In certain exemplary embodiments, methods for obtaining myofibers from mice, which may be extrapolated to other organisms, are described, (see for example Shefer and Yablonka-Reuveni) in addition, see the Example section.

Some embodiments herein concern administering one or more myofibers as discussed above, and/or providing a population of satellite stem cells. Such stem cells have been identified by the inventors and are described in detail herein. In particular, these cells are characterized as being self-renewing, obtainable from the side population (SP), can be positive for the markers Syndecan-4 and ABCG2, and in some embodiments, positive for the marker Sca1. In some embodiments, these cells may also be positive for the marker Pax7. These cells can form myotubes if cultured in vitro and exclusively engraft into the satellite cell niche in vivo. These cells are further described in the Examples Section. In myofiber cultures, satellite cells herein exhibit long-term BrdU label retention and divide asymmetrically to yield a quiescent "stem cell" daughter and an activated satellite cell daughter. During muscle regeneration, this subpopulation expands rapidly, eventually comprising ~50% of the satellite cell population before declining to levels found in uninjured muscle upon muscle repair. This behavior predicted for repair of tissue by adult stem cells is consistent with the "reserve" population originally discovered over a decade ago and consistent with that expected of an adult skeletal muscle stem cell. However, this is believed to be the first report of the ability to clearly identify and isolate these cells from among the side population of cells.

Reference to "stem cells", as used herein, refers to the term as it is generally understood in the art. For example, stem cells, regardless of their source, are cells that are capable of dividing and renewing themselves for long periods, are unspecialized (undifferentiated), and can give rise to (differentiate into) specialized cell types (e.g., they are progenitor or precursor cells for a variety of different, specialized cell types). "Long-term", when used in connection with stem cells, refers to the ability of stem cells to renew themselves by dividing into the same non-specialized cell type over long periods (e.g., many weeks, to many months, for example 3 months, to years to many years) depending on the specific type of stem cell. As discussed herein, phenotypic characteristics of long-term skeletal muscle stem cells referred to herein as satellite stem cells, are provided. Adult stem cells can include stem cells that can be obtained from any non-embryonic tissue or source, and typically generate the cell types of the tissue in which they reside. The term "adult stem cell" may be used interchangeably with the term "somatic stem cell". Certain embodiments herein concern stem cells identified and utilized from an adult subject.

In one aspect, a population of satellite stem cells can be isolated from myofibers or muscle tissue of a subject or a donor. In one aspect, the population of satellite stem cells can be isolated from the side population (SP) in bone marrow or a tissue. As used herein "side population" is known in the art as a subpopulation of cells in bone marrow and other tissues that were initially identified as being particularly effective at pumping out Hoechst 33342, a DNA-binding dye that binds preferentially to A-T rich regions of DNA using ABC (ATP-Binding Cassette) transporters which include p-glycoprotein and ABCG2 in human cells. Methods of identifying and isolating the side population are known in the art, see the Example section. In one aspect, populations of satellite stem cells can be provided from a cell line or established culture of cells. Some populations of satellite stem cells may be substantially pure or may contain other cells, including quiescent stem cell daughter cells, activated satellite cell daughter cells, and differentiated or partially differentiated myoblasts. Certain embodiments include populations of cells transplanted into a recipient that may contain at least 10% of the Syndecan-4/ABCG2 positive (which can also include Sca1-positive cells), self-renewing satellite cells of the invention, or at least 20%, or at least 30%, or at least 40%, or at least 50%, or at least 60%, or at least 70%, or at least 80%, or at least 90%, or at least 95% of the Syndecan-4/ABCG2 positive, self-renewing satellite cells.

In some embodiments, satellite stem cells provided herein (either in conjunction with a myofiber or as a separate population or culture of cells) can be genetically modified. In any of the embodiments described above, methods may further include genetically modifying the satellite stem cells to correct a genetic defect in the cells, genetically modifying the satellite stem cells to silence the expression of a gene, and/or genetically modifying the satellite stem cells to overexpress a gene. Combinations of modifications are contemplated.

In certain embodiments, satellite stem cells to be transplanted into an individual can be genetically modified prior to transplantation in order to correct functional defects in the cells in an individual (e.g., to correct defects in the gene encoding dystrophin associated with Duchenne muscular dystrophy), to enhance the ability of the cells to repair and regenerate muscle tissue, to treat blood-borne diseases such as hemophilia, or to treat any disease where delivery of a protein via the vasculature might be appropriate. In one embodiment, satellite stem cells described herein are genetically modified to express a heterologous protein for delivery to a non-muscle tissue or a tissue at or neighboring the site of transplantation of the cells. In accordance with this embodiment, the satellite cells can be used as vehicles to express a desired protein, such as a therapeutic protein. The satellite cells can be transplanted alone, or in conjunction with one or more myofibers. When using myofibers, the transplant can be implanted at any muscle site adjacent to the tissue or area to be treated, if the site to be treated is not a muscle. The muscle is highly vascularized and accordingly, it is an ideal location to deliver any gene, the expression product of which is to be released from the cells. Given the success of the methods disclosed herein regarding muscle repair and regeneration, modifying this technology to deliver any desirable heterologous protein in a site directed or systemic manner is readily contemplated.

In certain exemplary methods, genetically modified satellite stem cells of use herein can be a stem cell that has been modified (e.g., mutated or changed) within its genome and/or by recombinant technology (e.g., genetic engineering) from its normal (e.g., wild-type or naturally occurring) form. Cell can be modified by transfection with a recombinant nucleic acid molecule encoding a heterologous protein, and/or by deletion, insertion or inactivation of at least one gene in the cells.

Methods for successful introduction of a transgene into stem cells have been achieved in the art (see, for example, Chung et al., 2002); Takahashi et al., 1997; Hooper et al; Ma et al., 2003, each of which is incorporated by reference in its entirety). In addition, methods of genetically modifying myoblasts and satellite cells are known in the art and are described (e.g., Skuk et al., 2002).

Satellite stem cells, populations and cell lines disclosed herein can be cultured using methods known in the art. In some embodiments, cells are cultured under conditions that maintain the cells, but cause reduced or insubstantial differentiation of the cells prior to transplantation. One medium suitable for culture of animal cells or tissues can include any available medium which has been developed for culture of animal cells and particularly, mammalian cells, or which can be prepared in the laboratory with the appropriate components necessary for animal cell growth, such as assimilable carbon, nitrogen and micronutrients. Such a medium include, but are not limited to, a base medium, which is any base medium suitable for animal cell growth, including, but not limited to, F-12C Medium, Iscove's Modified Dulbecco's Medium (IMDM), Dulbecco's modified Eagles medium (DMEM), alpha MEM (Gibco), RPMI 1640, or any other suitable commercially available media. To the base medium, assimilable sources of carbon, nitrogen and micro-nutrients are added including, but not limited to, a serum source, growth factors, amino acids, antibiotics, vitamins, reducing agents, and/or sugar sources. It is noted that completed mediums include, but are not limited to, a base medium and many of the additional components necessary for animal cell growth are commercially available, and some media are available for particular types of cell culture. In addition, many serum-free media are available and may be particularly suited for the culture of satellite stem cells herein.

Accordingly, one embodiment relates to an isolated satellite cell, cell line, or population of cells as characterized in detail above. Also included are compositions comprising such cells, cell lines or populations of cells. For therapeutic methods, such compositions can include a pharmaceutically acceptable carrier, which includes pharmaceutically acceptable excipients and/or delivery vehicles (e.g., a myofiber), for delivering the cells, cell lines, or cell populations to an individual. As used herein, a pharmaceutically acceptable carrier refers to any substance suitable for delivering a therapeutic composition useful in the method of the present invention to a suitable in vivo site.

In certain embodiments of the method of the invention, when one or more myofibers are transplanted, the method includes a step of incubating the myofiber(s) in a medium comprising a fibroblast growth factor. In accordance with these embodiments, myofibers can be incubated, rather than cultured, meaning that the myofibers can be contacted with a suitable medium for a sufficient period of time suitable to allow the myofibers and associated cells to interact with any growth factors or medium components. Incubation should occur under conditions that preserves the association of satellite cells with the myofibers, and that does not reduce survival of satellite cells and/or myofibers. The incubation of the myofibers can be performed for an amount of time ranging from about 1 hour to up to 6 hours; to up to 12 hours, to up to 18 hours; to up to 24 hours or more, or any increment of time in between, in minute intervals. In certain embodiments, incubation can occur over a period from about 2 hours to about 6 hours, or from about 3 hours to about 4 hours. In some embodiments, incubation in a media formulation may not be performed prior to administering satellite cells and/or myofibers compositions to a subject. Some incubation period can occur at a temperature suitable for the culture of mammalian cells and tissues. Accordingly, incubation can be performed about 25° C. to about 45° C., about 30° C. to about 40° C.; 35° C. to about 40° C. and about 37° C.

Medium in which the myofibers can be incubated is any suitable medium for the culture of myofibers. For example, a suitable medium is F12-C medium (F12 medium with added calcium), although other suitable mediums for the culture of animal cells, muscle cells or stem cells can be used. Culture mediums and conditions for cells from various species (e.g., human) can be optimized readily by those of skill in the art and can be assessed, for example, by satellite cell behavior. As discussed above with regard to mediums for cell culture, to a base medium, assimilable sources of carbon, nitrogen and micro-nutrients are added including, but not limited to, a serum source, growth factors, amino acids, antibiotics, vitamins, reducing agents, and/or sugar sources. It is noted that completed mediums comprising a base medium and many of the additional components necessary for animal cell growth are commercially available. In one aspect, a complete media (e.g., F12-C media) is supplemented with horse serum (e.g., 5-20% serum, preferably 10-15%, and more preferably about 15%) and with a source of fibroblast growth factor (FGF).

According to embodiments disclosed herein, growth factors can be supplemented in the media for increasing viability of the cellular compositions disclosed. For example, a source of FGF (fibroblast growth factor) is contemplated. Any source of FGF, including, but not limited to, purified FGF protein, partially purified FGF protein, a supernatant or solution comprising FGF protein, or a cell line that produces and secretes FGF protein is contemplated. As used herein, reference to an isolated protein or polypeptide can (e.g., an FGF protein) include full-length proteins, fusion proteins, peptides derived from FGF, chimeric proteins, or any fragment (truncated form, portion) or homologue of such a protein. More specifically, an isolated protein can be a protein (including a polypeptide or peptide) that has been removed from its natural environment (e.g., that has been subject to human manipulation), and can include, but is not limited to, purified proteins, partially purified proteins, recombinantly produced proteins, membrane bound proteins, proteins complexed with lipids, soluble proteins, synthetically produced proteins, and isolated proteins associated with other proteins. As such, "isolated" does not reflect the extent to which the protein has been purified.

As used herein, the term "homologue" is used to refer to a protein or peptide which differs from a naturally occurring protein or peptide (i.e., the "prototype" or "wild-type" protein) by modifications, including minor modifications, to the naturally occurring protein or peptide, but which maintains the basic protein and side chain structure of the naturally occurring form. Such changes include, but are not limited to: changes in one or a few (e.g., 1, 2, 3, 4, 5, 6, 7, 8, 9 or 10) amino acid side chains; changes one or a few amino acids, including deletions (e.g., a protein or truncated form of the protein or peptide), insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein. Homologues can be the result of natural allelic variation or natural mutation.

In certain embodiments, FGF protein suitable for use in the incubation step can be an FGF protein (including fragments, homologues, and fusion proteins or chimeric proteins thereof) that bind to a fibroblast growth factor receptor (FGFR). In one embodiment, FGF protein binds to FGFR4. In one aspect, an FGF protein suitable for use in the invention is FGF-2, also referred to as basic fibroblast growth factor (bFGF). FGF-2 was one of the first FGFs to be identified and has been extensively studied. FGF-2 has been shown to be able to elicit various biological responses by binding to and activating specific cell-surface receptors called FGF receptor tyrosine kinases. Fibroblast growth factor biological activity is defined herein a measurable activity that is indicative of the biological activity of a naturally occurring fibroblast growth factor protein, as measured by an in vitro or in vivo assay. Such biological activities include, but are not limited to: promotion of cell proliferation (e.g., in a cell line such as MM14), repression of terminal differentiation in a cell (e.g., in a cell line such as MM14 or bovine brain capillary endothelial cells), promotion of angiogenesis in vivo (e.g., in a chicken chorioallantoic membrane assay), promotion of wound healing in vivo, promotion of osteogenesis on osteoblasts in an in vivo or in vitro assay, promotion of nerve outgrowth (primary neurons or neuronal cell lines). In vitro and in vivo assays for measuring FGF biological activity are known in the art.

It is contemplated herein that modified forms of FGF, such as the chimeric penetratin-FGF proteins described herein, may have different quantitative activity and specificity than a naturally occurring FGF protein. Some embodiments herein include FGF protein described in detail in U.S. Pat. No. 6,800,286, incorporated herein by reference in its entirety, which discloses a chimeric fibroblast growth factor (FGF) protein characterized by: (a) fibroblast growth factor biological activity in the absence of heparan sulfate; and, (b) an ability to enter a living cell in the absence of a receptor that binds to FGF. Any FGF fusion protein or chimeric protein with FGF biological activity is encompassed by the invention.

Certain embodiments include a source of FGF that can be included in the incubation medium at any concentration suitable for the number of myofibers and/or satellite stem cells being incubated, and suitable to interact with the myofibers and/or satellite stem cells and enhance engraftment and growth of the myofibers and/or satellite stem cells as described herein. For example, some suitable amounts of purified or recombinant FGF protein to add to an incubation medium for myofibers can ranges from about 0.1 nM to about 50 nM, including any increment in between in 0.1 nM increments, with about 5 nM being one exemplary amount. Those of skill in the art will be able to modify the incubation conditions and concentrations to accommodate the effective amount of different sources of FGF. Other growth factors alone or in combination with FGF are contemplated herein.

In one embodiment, alternate growth factors are used in place of the FGF described above. For example, hepatocyte growth factor (HGF) or tumor necrosis factor-α (TNF-α) are considered of use for incubation of compositions disclosed herein alone or in combination with FGF. Any growth factor or other cytokine that duplicates or enhances the activity of FGF with respect to the myofiber engraftment described herein is contemplated.

Certain embodiments herein may include injuring or initiating muscle regeneration of the donor myofiber and also the site of muscle transplant in the recipient. Injuring donor myofiber is not an essential step to the method, and can be omitted, if desired. With regard to the site of the muscle transplant in the recipient, while one may directly cause injury to the muscle tissue to initiate regeneration processes prior to transplant, this may not be necessary in practice if muscle tissue regeneration is already ongoing at the site. For example, as an alternative to actively injuring the site of muscle transplant in the recipient, the recipient tissue can be any muscle tissue that is undergoing regeneration. Accordingly, instead of actively injuring the recipient site of transplant, regeneration at the site can be induced, for example, by natural occurrences, including, but not limited to, disease-induced muscle injury or regeneration (e.g., as a result of muscular dystrophy), any type of injury to the muscle tissue (e.g., trauma, athletic injury, etc.), and/or regenerating muscle tissue due to aging processes.

In some embodiments, if active injury to the recipient tissue is performed (e.g., as opposed to transplanting into a tissue that is has some injury or defect due to disease or aging and is naturally undergoing regeneration), this can be performed using any technique that causes damage to the muscle fibers (both donor and recipient), without killing the satellite cells associate with the fibers, and in one aspect, without completely killing the myofiber itself During active injury, however, the myofibers may die fairly quickly; however, the niche needed to effect the successful transplantation is believed to be transient in nature. Suitable techniques for actively injuring the muscle tissue include, but are not limited to, exposure of the myofibers to $BaCl_2$ (e.g., injection or incubation of myofibers in 1.2% $BaCl_2$), the use of other myonecrotic agents, including, but not limited to, snake toxins cardiotoxin and notexin, forced-lengthening or transection injury (suitable for the recipient site). As discussed above, these embodiments can also be avoided by simply choosing a site of transplantation where the muscle tissue is damaged, injured and/or already undergoing regeneration.

Some embodiments herein concern implanting donor myofiber (and/or the culture and/or satellite stem cells) at the site of muscle transplant. Transplantation of muscle fibers in mammalian species are known in the art and have been described in the Examples and elsewhere in the art (e.g., see Collins et al., 2005). In some embodiment, procedures previously disclosed differ from that used herein in that the fibers are implanted into irradiated muscle, whereby injury to the muscle occurs after transplant. Myofibers and/or satellite stem cells can be simply injected into the muscle at the site of transplantation. In certain instances, there is significant flexibility with respect to the timing of myonecrotic injury (if used in lieu of selection of injured/regenerating tissue) and the injection or other implantation of the fibers.

In one embodiment, a single myofiber, prepared as described herein and injected once, may be sufficient to repair and regenerate muscle at a site of muscle damage. Accordingly, administration performed on a subject any number of times to achieve a desired result of repair and/or regeneration of muscle tissue, repair of a genetic defect in muscle, or release of desired proteins/compounds from an implanted cell is contemplated herein. The times required may be a single time, a couple of times, or multiple times or the method may be repeated as determined to be necessary by a health care provider.

In some embodiments, the number of myofibers and/or satellite stem cells to be implanted (administered) are any suitable number, and may vary depending on the source of the donor tissue, the size of the recipient site to be treated or repaired, the individual's health, or the state of the myofibers to be transplanted, among other considerations. Accordingly, the method includes the implantation (administration) of at least one myofiber per single site in a host recipient, and can include the implantation (administration) of 2, 3, 4, 5, 6, 7, 8, 9, 10, 11, 12, 13, 14, 15, 16, 17, 18, 19, 20, or more myofibers and/or satellite stem cells per single site, including any additional number of fibers, in whole number increments (e.g., 21, 22, 23 . . . ), up to 15, 50, 75, 100, or more myofibers and/or satellite stem cells per single site. As discussed above, administration of a single myofiber typically results in the administration of about 15-20; 20-50; 50-100 or more satellite cells associated with that myofiber, although these numbers may vary depending on the donor source, method of isolation, and methods of incubation and implantation. Certain embodiments concern, between about 100 and about 500 satellite cells per myofiber are administered (as cells associated with the myofiber), and about 100 to 1000 satellite cells per myofiber, and more preferably between about 500 satellite stem cells. It will be appreciated that it is not necessary to provide a specified number of cells per myofiber if the myofibers are handled as described herein, since each myofiber is naturally associated with satellite cells. Accordingly, the number of satellite cells per myofiber will be expected to naturally vary, but is typically found within the ranges disclosed herein. In addition, it is contemplated that satellite cells may be administered to a subject as a composition not associated with myofibers.

When isolated cells or a population or culture thereof are administered in the absence of myofibers, the number of cells to be administered at the site of implantation is preferably between about 1000 cells and about 50,000 cells, or between about 2500 cells and about 25,000 cells, or between about 5000 cells and about 15,000 cells, and in one aspect, about 10,000 cells. Administration of about 10,000 cells would approximate the administration of about 10 myofibers (containing about 200 cells). Accordingly, the use of myofibers according to the method of the invention is more efficient. However, administration of purified populations of the satellite stem cells described herein may reduce the total number of cells required for administration. One of skill in the art will readily be able to determine the appropriate number of cells for administration. It is noted that the numbers described above are typical for smaller mammals and may be suitable for larger animals; however, in practice, the selection of actual cell numbers to be transplanted may be more typically based on the mass of the animal, rather than an absolute number of cells.

In one embodiment, when isolated cells or a population or culture thereof are administered in the absence of myofibers, cells can be administered in conjunction with a pharmaceutically acceptable carrier, which may include a composition of growth factors, such as those present as a result of implantation with the myofiber compositions disclosed herein.

In another embodiment, FGF can be administered at the site of the implantation in conjunction with the myofibers and/or cells. In one aspect of this embodiment, the FGF is a chimeric fibroblast growth factor (FGF) protein as described in U.S. Pat. No. 6,800,286, characterized by: (a) fibroblast growth factor biological activity in the absence of heparan sulfate; and, (b) an ability to enter a living cell in the absence of a receptor that binds to FGF.

Methods and uses directed to the repair or regeneration of muscle tissue according to the invention are intended for use in any individual, but are particularly useful in patients suffering from a muscle disorder or disease, such as any of the muscular dystrophies, including, but not limited to, Duchenne muscular dystrophy, Becker muscular dystrophy, or any neuromuscular degenerative disease, any loss of muscle function due to disease, and any muscle damage or decrease in mass or function due to the aging process. In these embodiments, the methods are used not only to repair or regenerate muscle tissue in the diseased individual, but can also be used to correct or complement a genetic defect in the muscle cells of the individual by providing genetically modified satellite cells as described herein.

Methods disclosed herein are also useful for repairing injured or damaged muscles in any individual who has been injured, such as an athletic injury, injury due to an accident (e.g., trauma), or injury due to another procedure (e.g., surgery). The muscles that can be repaired are not limited to the larger skeletal locomoter muscles, but include, without limitation, any small muscles, including sphincter muscles, for example. Accordingly, embodiments herein are useful for the treatment of disorders related to sphincter muscles, including a variety of gastrointestinal and urogenital disorders (e.g., neuro-urogenital disorders).

Methods herein may also be useful for enhancing muscle growth in an individual, including a healthy individual.

In some embodiments, methods herein may also be of use where it is desired to use the muscle as a vehicle for gene delivery or more specifically, exogenous protein or drug delivery, by genetically modifying the cell to express a protein or agent that can be expressed and possibly secreted by the muscle cells once implanted. The proteins and uses for such cells are substantial, and can include provision of various growth factors, therapeutic agents, and the like, either systemically or at a targeted site by virtue of the extent and site(s) of the implantation of the cells.

Accordingly, although one embodiment of the invention envisions correcting genetic defects that cause a disease in an individual, the invention is not limited or necessarily intended to "cure" or completely repair a defect in an individual. Rather, the methods of the invention are generally useful for providing any benefit to an individual through enhanced muscle growth, repair and/or regeneration, including a physiological benefit and a psychological benefit.

Methods disclosed herein can be performed, without limitation, on any member of the Vertebrate class, Mammalia, including, without limitation, primates, livestock and domestic pets (e.g., a companion animal). In some embodiments, a subject can be a human individual. The term "individual" can be interchanged with the term "subject" or "patient" and refers to the subject of a method according to the invention. Accordingly, an individual can include a healthy, normal (non-diseased, non-injured) individual, but is most typically an individual who has a muscle injury or a disease of the muscle tissue, or who is at risk of developing a hereditary disease of the muscle tissue.

In some embodiments, administration of cellular compositions disclosed for delivering a compound and/or gene to a site in a subject having a condition can include methods for regulating the gene or compound such as expression or regulation of the gene. It is also contemplated herein that compositions herein may include a microarray, gel, microsphere or other timed-release or slow-release technology. Regulatory means are also contemplated of use for gene expression of a genetic element introduced to a subject such as promoters, inducers, and other regulatory components.

Proteins and Polypeptides

Some embodiments pertain to isolated proteins, and biologically active portions thereof, as well as polypeptide fragments. In one embodiment, the native polypeptide can be isolated from cells or tissue sources by an appropriate purification scheme using standard protein purification techniques. In another embodiment, polypeptides contemplated herein are produced by recombinant DNA techniques. Alternative to recombinant expression, a polypeptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium. When the protein is produced by chemical synthesis, it is preferably substantially free of chemical precursors or other chemicals. For example, such preparations of the protein have less than about 30%, 20%, 10%, 5% (by dry weight) of chemical precursors or compounds other than the polypeptide of interest.

Varients of the polypeptides are contemplated herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein may inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

In one embodiment, fusion polypeptides can be produced by recombinant DNA techniques. Alternative to recombinant expression, a fusion polypeptide of the invention can be synthesized chemically using standard peptide synthesis techniques. In addition, a fusion polypeptide disclosed herein can include a pharmaceutically acceptable carrier, excipient or diluent. Other Agents Any of the embodiments detailed herein may further include one or more a therapeutically effective amount of anti-microbial drugs, anti-inflammatory agent, immunomodulatory agent, or immunosuppressive agent or combination thereof. Examples of anti-bacterial agents include, but are not limited to, penicillins, quinolonses, aminoglycosides, vancomycin, monobactams, cephalosporins, carbacephems, cephamycins, carbapenems, and monobactams and their various salts, acids, bases, and other derivatives.

Anti-fungal agents contemplated of use herein can include, but are not limited to, caspofungin, terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide.

Anti-viral agents contemplated of use herein can include, but are not limited to, valgancyclovir, amantadine hydrochloride, rimantadin, acyclovir, famciclovir, foscamet, ganciclovir sodium, idoxuridine, ribavirin, sorivudine, trifluridine, valacyclovir, vidarabin, didanosine, stavudine, zalcitabine, zidovudine, interferon alpha, and edoxudine.

Immunomodulatory agents can include for example, agents which act on the immune system, directly or indirectly, by stimulating or suppressing a cellular activity of a cell in the immune system, (e.g., T-cells, B-cells, macrophages, or antigen presenting cells (APC)), or by acting upon components outside the immune system which, in turn, stimulate, suppress, or modulate the immune system (e.g., hormones, receptor agonists or antagonists, and neurotransmitters); other immunomodulatory agents can include immunosuppressants or immunostimulants. Anti-inflammatory agents can include, for example, agents which treat inflammatory responses, tissue reaction to injury, agents which treat the immune, vascular, or lymphatic systems or combination thereof.

Anti-inflammatory or immunomodulatory drugs or agents contemplated of use herein can include, but are not limited to, interferon derivatives, e.g., betaseron, β-interferon; prostane derivatives, iloprost, cicaprost; glucocorticoids such as cortisol, prednisolone, methylprednisolone, dexamethasone; immunsuppressive agents such as cyclosporine A, FK-506, methoxsalene, thalidomide, sulfasalazine, azathioprine, methotrexate; lipoxygenase inhibitors, e.g., zileutone, MK-886, WY-50295, SC-45662, SC-41661A, BI-L-357; leukotriene antagonists; peptide derivatives for example ACTH and analogs; soluble TNF (tumor necrosis factor)-receptors; TNF-antibodies; soluble receptors of interleukines, other cytokines, T-cell-proteins; antibodies against receptors of interleukins, other cytokines, and T-cell-proteins.

Pharmaceutical Compositions

Embodiments herein provide for administration of compositions to subjects in a biologically compatible form suitable for pharmaceutical administration in vivo. By "biologically compatible form suitable for administration in vivo" is meant a form of the active agent (e.g. pharmaceutical chemical, protein, gene, antibody, or anti-viral agent) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regima may be adjusted to provide the optimum therapeutic response.

In one embodiment, the compound (e.g. pharmaceutical chemical, protein, gene, antibody, or anti-viral agent) may be administered to a subject in need thereof subcutaneously, intravenously, by oral administration, inhalation, transdermally, intravaginally, topically, intranasally, rectally or a combination thereof. Depending on the route of administration, the active compound may be coated in a material to protect the compound from the degradation by enzymes, acids and other natural conditions that may inactivate the compound. In a preferred embodiment, the compound may be orally administered. In another preferred embodiment, the compound may be administered intravenously. In one particular embodiment, the compound may be administered intranasally, such as inhalation.

A compound may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used. In all cases, the composition can be sterile and can be fluid to the extent that easy syringability exists. It might be stable under the conditions of manufacture and storage and may be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of microorganisms can be achieved by heating, exposing the agent to detergent, irradiation or adding various antibacterial or antifungal agents.

Sterile injectable solutions can be prepared by incorporating active compound (e.g. a compound that has reduced or no significant serine protease inhibitor activity) in the required amount in an appropriate solvent with one or a combination of ingredients enumerated above, as required, followed by filter sterilization.

Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art.

Solutions of the active compounds as free-base or pharmacologically acceptable salts can be prepared and suitably mixed with for example, a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms. Prolonged absorption of the injectable or ingestible compositions can be brought about by compositions of agents delaying absorption, for example, aluminum monostearate, gelatin or the like. In other embodiments, a composition contemplated herein can be in the form of a slow or time-released particle or capsule such as microparticles, for example, microbeads or a microgel. In accordance with these embodiments, a microparticle can contain a composition disclosed herein and once the microparticles are introduced to a subject in need thereof the composition can be released upon targeting a specific region, in timed intervals or as the microparticles degrade. These methods are known in the art and are contemplated herein.

Therapeutic agents may be formulated within a mixture to include about 0.0001 to 1.0 milligrams, or about 0.001 to 0.1 milligrams, or about 0.1 to 1.0 or even about 1 to 10 gram per dose. Single dose or multiple doses can also be administered on an appropriate schedule for a predetermined condition.

In another embodiment, nasal solutions or sprays, aerosols or inhalants may be used to deliver the compound of interest. Additional formulations that are suitable for other modes of administration include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. In certain embodiments, oral pharmaceutical compositions can include an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

A pharmaceutical composition may be prepared with carriers that protect active ingredients against rapid elimination from the body, such as time-release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others are known.

Pharmaceutical compositions are administered in an amount, and with a frequency, that is effective to inhibit or alleviate side effects of a transplant and/or to reduce or prevent rejection. The precise dosage and duration of treatment may be determined empirically using known testing protocols or by testing the compositions in model systems known in the art and extrapolating therefrom. Dosages may also vary with the severity of the condition. A pharmaceutical composition is generally formulated and administered to exert a therapeutically useful effect while minimizing undesirable side effects. In general, an oral dose ranges from about 200 mg to about 1000 mg, which may be administered for example, 1 to 3 times per day.

It is contemplated that, for a particular subject, specific dosage regimens may be adjusted over time according to need. A preferred dose for administration can be anywhere in a range between about 0.01 mg and about 100 mg per ml of biologic fluid of treated subject. In one particular embodiment, the range can be between 1 and 100 mg/kg which can be administered daily, every other day, biweekly, weekly, monthly etc. In another particular embodiment, the range can be between 10 and 75 mg/kg introduced weekly to a subject.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent.

Liposomes can be used as a therapeutic delivery system and can be prepared in accordance with known laboratory techniques. In addition, dried lipids or lyophilized liposomes prepared as previously described may be reconstituted in a solution of active agent (e.g. nucleic acid, peptide, protein or chemical agent), and the solution diluted to an appropriate concentration with a suitable solvent known to those skilled in the art. The amount of active agent encapsulated can be determined in accordance with standard methods.

Kits

In some embodiments, kits disclosed herein concern for use with the methods described herein. The kits may include, one or more suitable containers, one or more myofiber and/or satellite stem cell compositions. In various embodiments, such kits may contain additional components of use for culturing the compositions or using the compositions for administration to a subject in need of such a treatment. In some embodiments, kits may be used for harvesting and/or culturing and/or delivering compositions contemplated herein.

The kits may further include suitably aliquoted compounds or other agents for delivery to a subject in need thereof. For example, a compound to be introduced using cellular compositions disclosed herein is contemplated as one or more kit components. The components of the kits may be packaged either in aqueous media or in lyophilized form.

The container means of the kits will generally include at least one vial, test tube, flask, bottle, syringe or other container means, into which the probes and/or primers may be placed, and preferably, suitably aliquoted. Where an additional component is provided, the kit will also generally contain additional containers into which this component may be placed. The kits of the present invention will also typically include a means for containing probes, primers, and any other reagent containers in close confinement for commercial sale. Such containers may include injection or blow-molded plastic containers into which the desired vials are retained.

The embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

EXAMPLES

Example 1

In one example use of an exemplary method to successfully transplant muscle tissue into a host recipient is described.

In this experiment, the following general protocol was used. Approximately 1-10 muscle fibers (in this experiment, the muscle fibers were from a GFP transgenic mouse, so that the donor tissue and cells could be tracked throughout the engraftment process). Since a typical myofiber contains about 10-20 associated satellite cells, the 3 fiber graft contains approximately 30-60 associated satellite cells. The fibers are transplanted into the recipient mouse within about 6 hours post isolation from the donor. Prior to implantation, the muscle fibers are handled in a manner that preserves the association of the satellite cell with the muscle fiber, which includes incubation of the fibers in medium containing growth factors that include a source of fibroblast growth factor. After incubation, the myofibers and the recipient muscle are injured using a technique that causes damage to the fibers, but does not kill the satellite cells associated with the myofibers. This step can be performed simultaneously with the transplant, such as by injecting fibers in a $BaCl_2$ solution into the host (the $BaCl_2$ causes the above-described injury to both donor and recipient muscle tissue).

In one exemplary experiment, muscle transplantation was performed as follows (see for example, FIG. 1).

Protocol for Mouse
1. Kill donor mouse via cervical dislocation
2. Dissect muscles from both hind limbs into PBS;
   a. Remove fascia and fat deposits from dissected muscles;
   b. Cutting lengthways, cut dissected muscles into small pieces and transfer to Ham's F12 media without horse serum during interim period.
3. Transfer prepared muscles from individual hind limbs into 15 ml conical with 9 mls of pre-warmed Ham's F12 media without horse serum and 1 ml of collagenase (Worthingtonn, Inc).
4. Incubate tubes for about 1 hour at about 37° C.—gently rock the tubes approximately every 15 minutes to aid in fiber separation.
5. Pour contents of 15 ml conical tubes into individual uncoated plates with 50 mls of pre-warmed Ham's F12 media with 15% horse serum and FGF2 (1 ml of 56 nM per 50 ml of media).
6. Under a dissecting microscope pick individual viable fibers using a glass pipette and transfer to an uncoated plate containing 50 mls of pre-warmed Ham's F12 media with 15% horse serum and FGF.
7. Incubate fibers for 3-4 hrs at 37° C.
8. Prepare an uncoated plate containing 50 mls of sterile 1.2% Barium Chloride solution in 0.9% Saline.
9. Draw up approximately 20 fibers for a single use using a 27 g ½ Tuberculin Syringe and inject contents into 1.2% $BaCl_2$ plate.
10. Redraw 10 muscle fibers into approximately 80 μl of 1.2% $BaCl_2$.
11. Anesthetize host mouse with isofluorane gas.
12. Inject fibers in 80 μl 1.2% $BaCl_2$ into right TA muscle of the anesthetized host mouse using the visible associated tendon of the TA as a guide into the muscle.

Efficient engraftment indicates that the satellite cells maintain contact with their native environment or niche. Thus, a procedure where isolated myofibers are engrafted along with their associated satellite cells and satellite stem cells was used. A single myofiber frequently has between 15 and 20 associated satellite cells. Grafts are injected simultaneously with muscle injury. The following figures demonstrate efficiency of the injections, the time frame of appearance of cells and the changes in the muscle following engraftment.

Referring to FIG. 2, in one experiment, the tibialis anterior (TA) muscle was removed 60 days (d) following engraftment of 3 muscle fibers. The contralateral muscle that was not injured or subjected to engraftment is shown as a control. The engrafted muscle is approximately 50% larger in mass than the contralateral side. Subsequent experiments performed suggest that transplanted TA muscles retain the increase in mass for at least 18 months. Engraftment is enhanced by FGF2 addition (FIG. 2B) where injury with either $BaCl_2$ or cardiotoxin is enhanced by addition of FGF2 to the myofibers prior to transplantation.

Figure 3A:
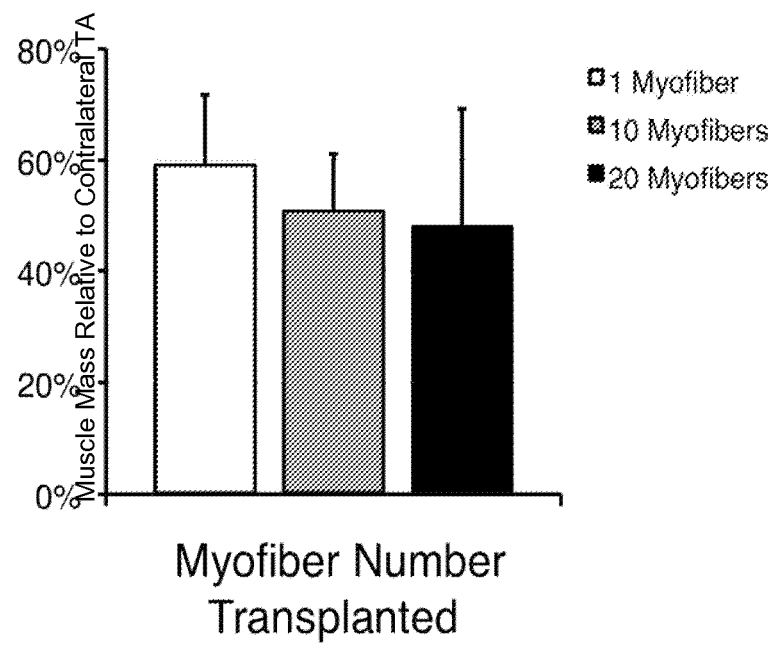
FIG. 3A represents an exemplary histogram illustrating yield in muscle mass from transplantation of 1, 5, 10 and 20 myofibers.
Figure 3B:
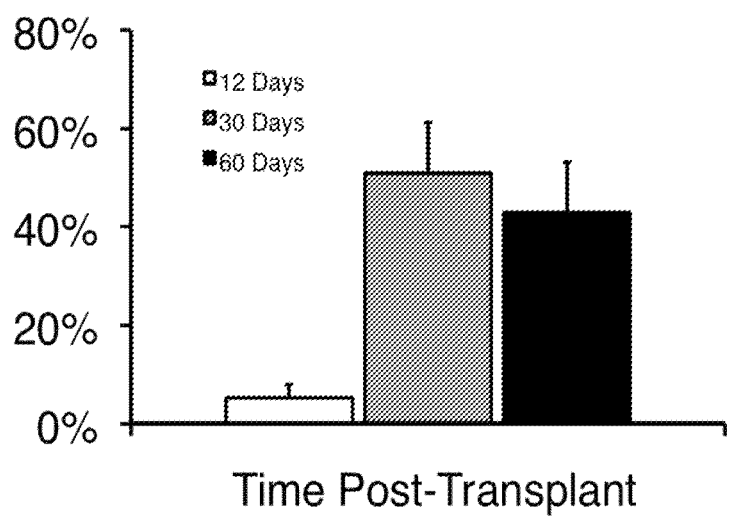
FIG. 3B represents an exemplary histogram illustrating increase of muscle mass in transplanted myofibers over time.
Figure 4A:
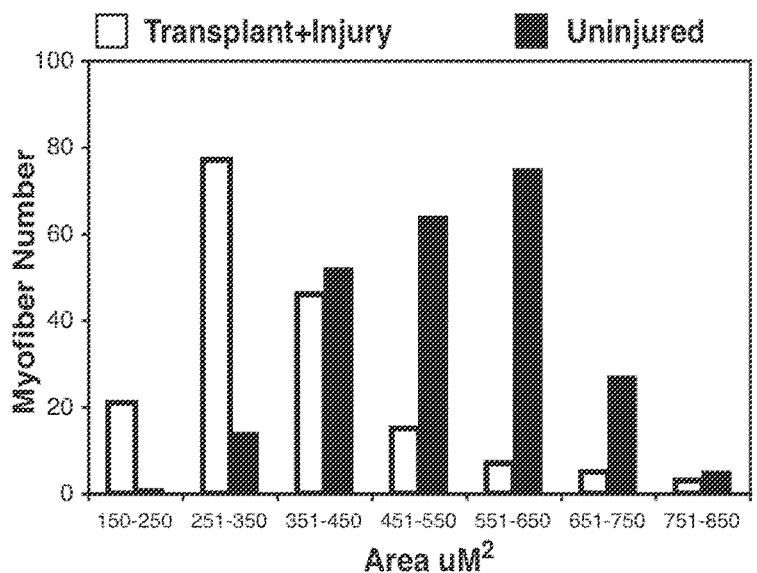
FIG. 4A represents an exemplary histogram illustrating the frequency of myofiber area in transplanted and control.
Figure 4B:
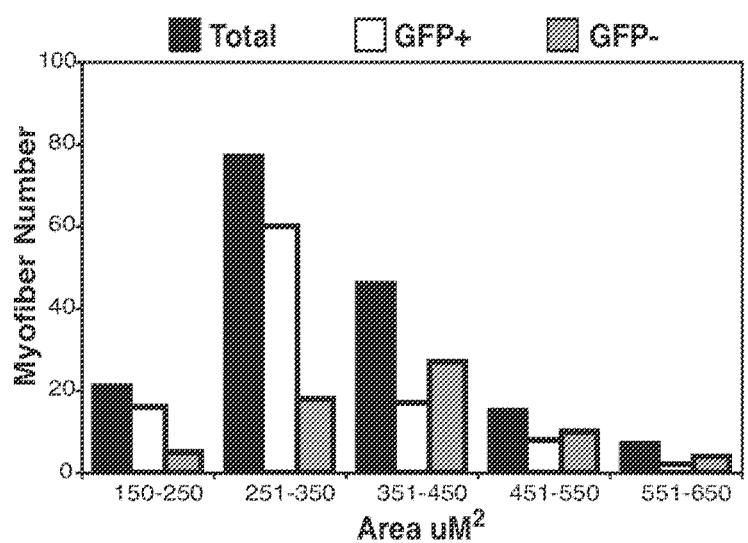
FIG. 4B represents an exemplary histogram comparing the area of myofibers containing donor cells with host.
Figure 5:
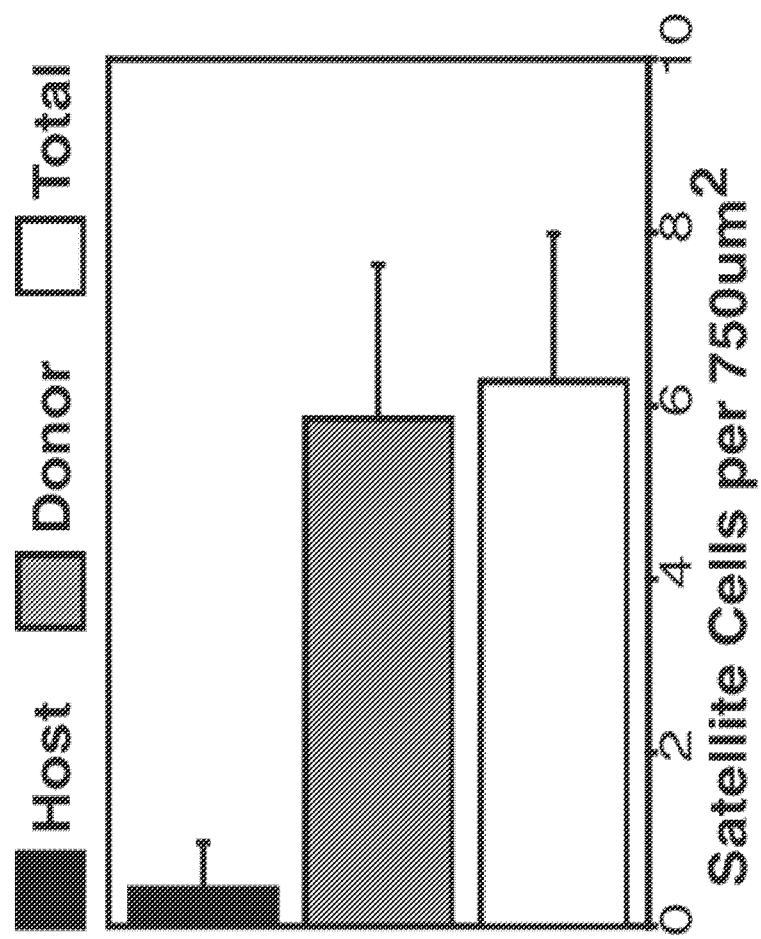
FIG. 5 represents an exemplary histogram illustrating the number of donor and host satellite cells in transplanted muscle.

FIG. 3 illustrates that an average area of myofibers that receive donor cells is smaller than the host myofibers that did not receive an engraftment. The engrafted myofibers appear smaller yet the muscle tissue is much larger. This discrepancy is accounted for by an increase in the total number of fibers or hyperplasia in the host mouse. The mass increase in the transplanted tibialis anterior muscle is due to an overall increase in the number of muscle fibers and appears not to be not due to fiber hypertophy that often occurs upon resistance exercise. FIG. 4 illustrates that the host tissue is populated by donor satellite cells that exceed the host satellite cells by approximately 5 to 1.

Example 2

The following example demonstrates that a self-renewing population of cells can be engrafted into skeletal muscle using methods disclosed herein.

In this example, a self-renewing population of cells can be considered to have the properties of an adult stem cell. To determine whether such a population can be engrafted into skeletal muscle using the method of the present invention, for this two-step transplant (see FIG. 6), ten myofibers were harvested from a GFP-positive mouse and transplanted into a host TA muscle with a simultaneous injury as performed previously (see Example 1). The primary recipient TA muscle was harvested 30 d later and 10 myofibers transplanted into a secondary recipient. The muscles were analyzed for donor contribution.

Figure 6:
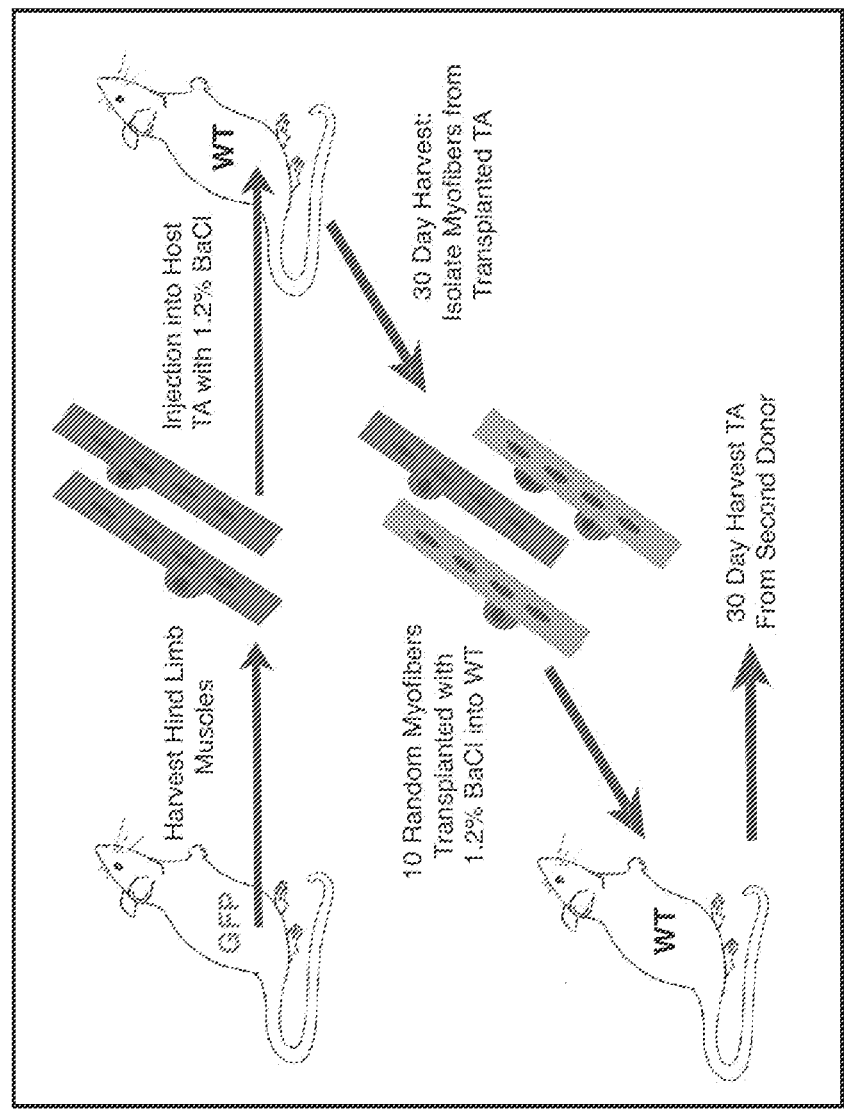
FIG. 6 represents an exemplary schematic illustrating serial transplantation of myofibers.
Figure 7A:
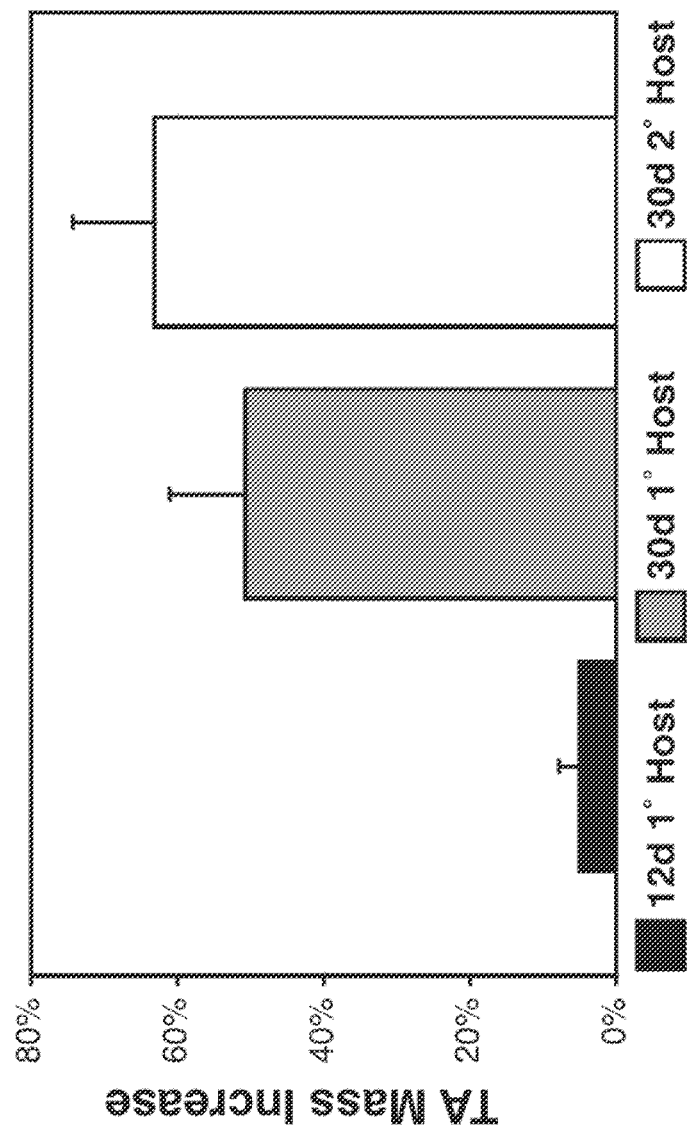
FIG. 7A represents an exemplary histogram comparing mass increase in primary and secondary transplants.
Figure 7B:
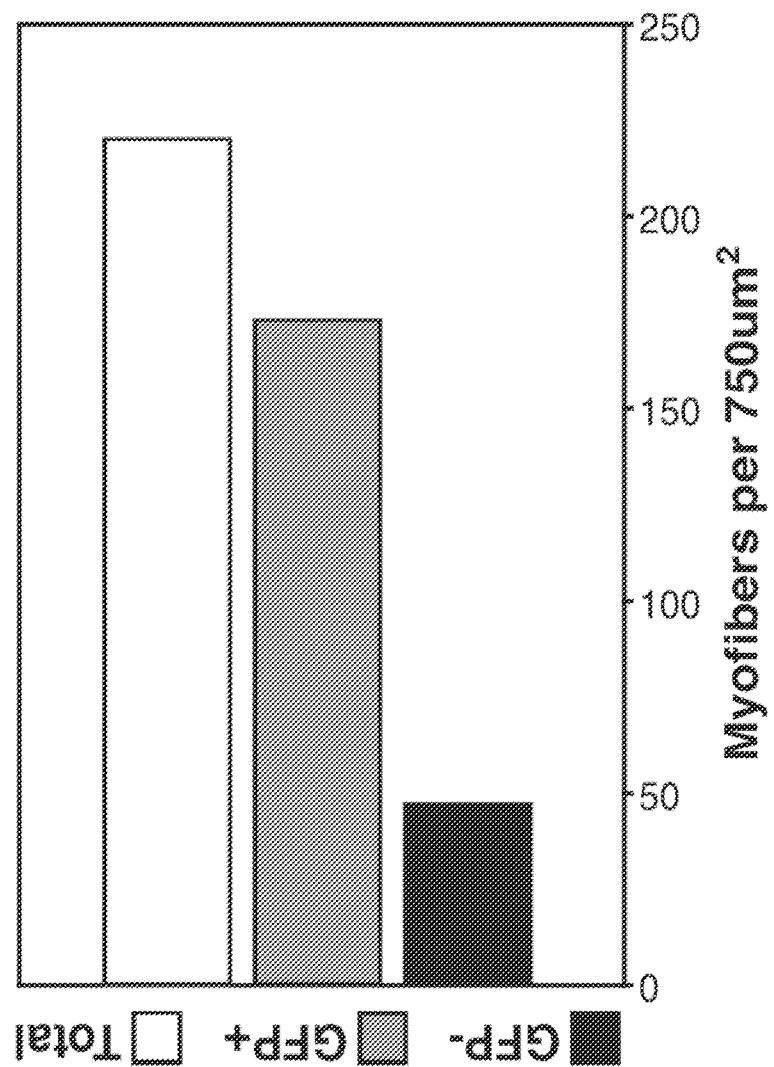
FIG. 7B represents an exemplary histogram comparing the number of host myofibers in the secondary transplant with and without donor cell contribution.
Figure 8:
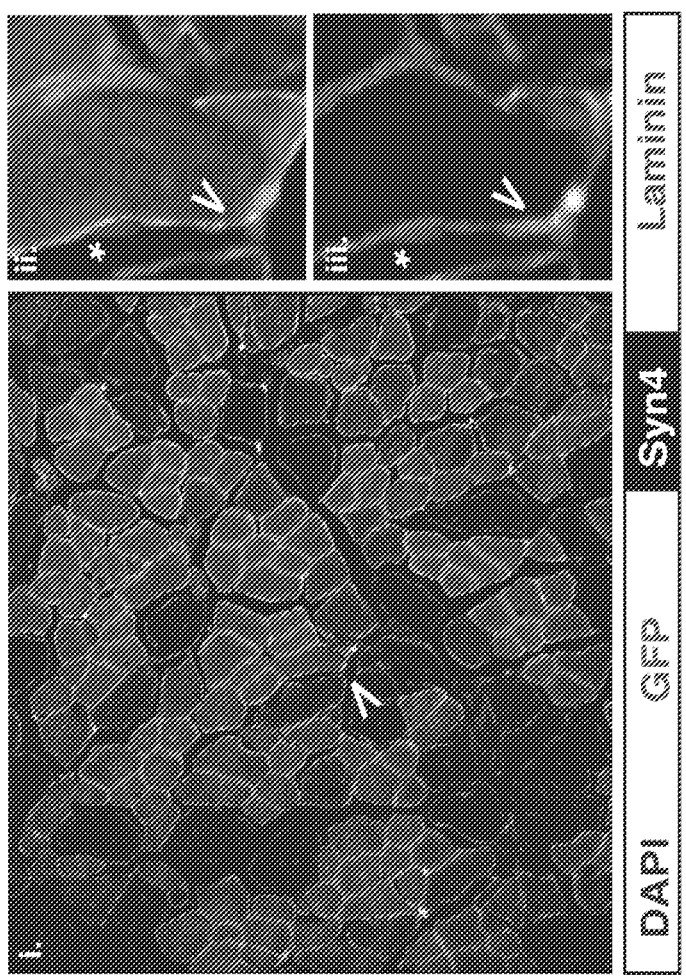
FIG. 8 represents an exemplary digital image illustrating a section from a secondary transplantation and identification of donor satellite cells.

FIG. 6 illustrates an exemplary schematic for a serial transplantation experiment designed to indicate presence of self-renewing stem cells. FIGS. 7A and 7B illustrate that the number of engrafted myofibers in the secondary recipient exhibit donor cell engraftment levels similar to or better than the primary recipient demonstrating that donor satellite cells retain their engraftment capacity when passaged through a primary recipient. FIG. 8 illustrates presence of donor satellite cells in the secondary recipient. This is evidence in support that these donor satellite cells possess the capacity to self-renew and provide a permanent population of self-renewing stem cells in a subject.

Example 3

The following example illustrates an exemplary method for successfully transplanting purified muscle stem cells into a host recipient.

Here, purified the muscle stem cells have been demonstrate to be removed from their environment and successfully transplanted. Cells, in this example, are treated identically to the myofibers after purification. Efficiency of the muscle stem cell transplant can be less than the myofibers but has been successfully performed with injection of 2500 cells.

In one specific experiment, muscle transplantation was performed as follows (see FIG. 1).
Protocol for Mouse
1. Kill mouse with cervical dislocation
2. Remove skin from one hindlimb and cut the muscle off in large chunks with scissors. Place the tissue into a glass Petri dish working reasonably quickly so tissue doesn't get too dry.
3. Once all of the tissue from the leg is removed, chop up the muscle with for example #10 scalpels until an evenish color is visible.
4. Transfer the minced tissue to a 50 ml conical tube with 9 ml F12-C (without serum) and keep on ice while processing the other limb(s).
5. Repeat steps 2-4 for the other hindlimb(s) to end up with 2 conical tubes/mouse (1 hindlimb/10 ml 1× collagenase). Also, give all the tubes a quick vortex each time another tube is added to the ice bucket.
6. To each tube add 1 ml 10× collagenase I (10× concentration is 4000 U/ml) and mix. Note that 2 separate types of collagenase are obtained—1 marked M for mass preps and 1 marked F for fiber preps.
7. Incubate tubes at 37° C. for 1 hour with quick vortexing about every 10 minutes
8. Filter the tissue through a 70 μm filter then a 40 μm filter. If there are a lot of chunks and the filter clogs I just use additional 70 μm filters.
9. Following cell isolation, resuspend in 1 ml F12-C+15% HS/mouse. This always yields slightly more than 1 ml. Use the "excess" to aliquot out 100 μl for each control. Initially controls include: unstained cells, each 2° Ab individually (e.g. for chick S4 this would be chick-488 only), all the 2° Abs together, each 1°+2° Ab combination (e.g. chick-S4+chick-488 together) for all the 1°+2° Abs together use 1 ml sample for sorting.
10. Add the appropriate 1° Abs to their respective tubes
11. Incubate the cells at 4° C. on the rotator for 45 min.
12. Keeping the cells on ice or at 4° C. from here on out, spin the cells at 2 G 5 min at 4° C.
13. Resuspend the cells in appropriate volumes (1 ml or 100 μl) F12-C+15% HS.
14. Add the appropriate 2° Abs to their respective tubes.
15. Store the cells on ice for transport.
16. Prior to putting samples on the MoFlo add Dapi (10 μl/ml of 0.1 mg/ml solution)
17. Set the background gates using the 2° Abs and sort by gating for cells size on FSC/SSC, Dapi negative (often this is very loud and doesn't give the traditional 2 peaks seen with cell culture, but take the low fluorescing cells from this channel), doublet exclusion and then populations of interest for 1° Abs.
18. Centrifuge cells at 1000×g and resuspend in Ham's F12 with 15% horse serum and FGF for 4 h
19. Centrifuge cells at 1000×g and resuspend in 80 μl of 1.2% $BaCl_2$.
20. Anesthetize host mouse with isofluorane gas.
21. Inject cells in 80 μl 1.2% $BaCl_2$ into right TA muscle of the anesthetized host mouse using the visible associated tendon of the TA as a guide into the muscle.

Figure 11:
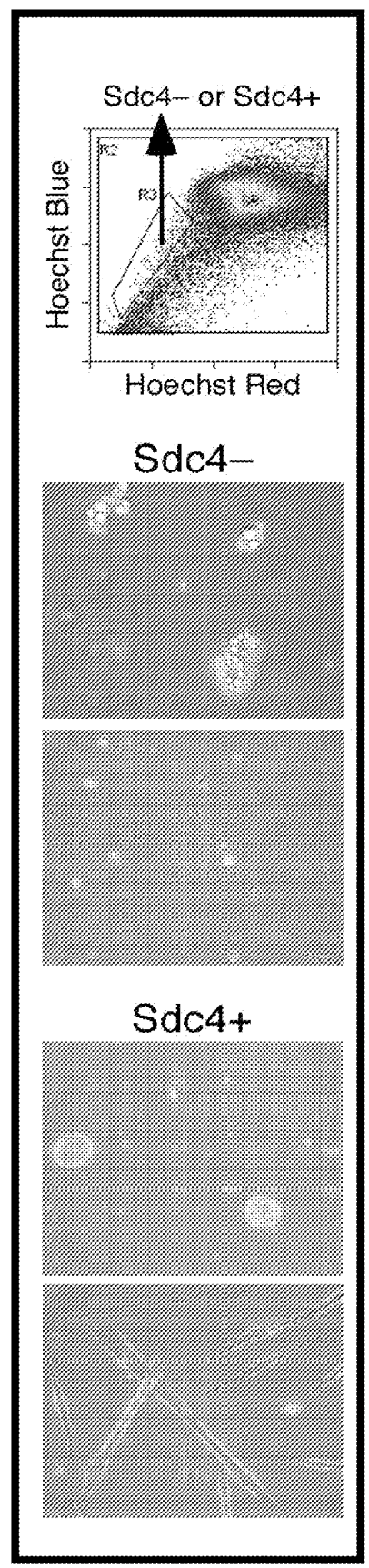
FIG. 11 illustrates an example of muscle stem cells expressing Syndecan-4 form myotubes in culture.

FIG. 9A illustrates that the entire population of cells in hindlimb muscle, approximately 20%, express Syndecan-4 and that these cells do not express blood cell markers. FIGS. 9B and 9C illustrate that the Syndecan-4 population of cells is heterogeneous and that a subpopulation of these cells expresses ABCG2 and Sca1. FIG. 10 illustrates that the ABCG2 and Sca1 expressing subpopulation of Syndecan-4 expressing cells engrafts efficiently into host muscle in the absence of the myofiber. These figures also demonstrate that this subpopulation preferentially becomes satellite cells in the host myofiber suggesting that the ABCG2, Sca1 and Syndecan-4 expressing subpopulation represents a muscle stem cell. FIG. 11 illustrates that Syndecan-4 expressing subpopulation of SP cells in muscle can differentiate into muscle in culture.

Example 4

The following example illustrates support for treating a muscular dystrophy using tissue transpantation.

Figure 12A:
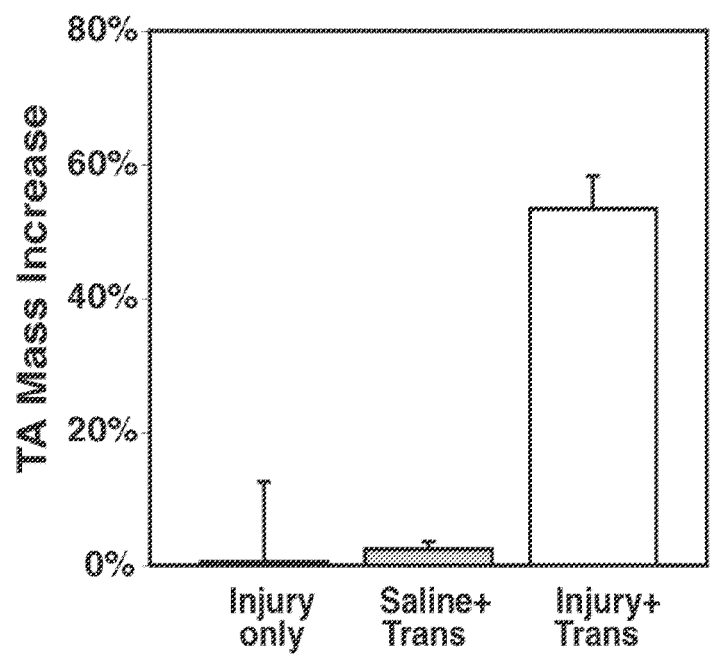
FIG. 12A represents an exemplary histogram illustrating mass increase occurs in transplanted mdx muscle when injury accompanies the transplant.
Figure 12B:
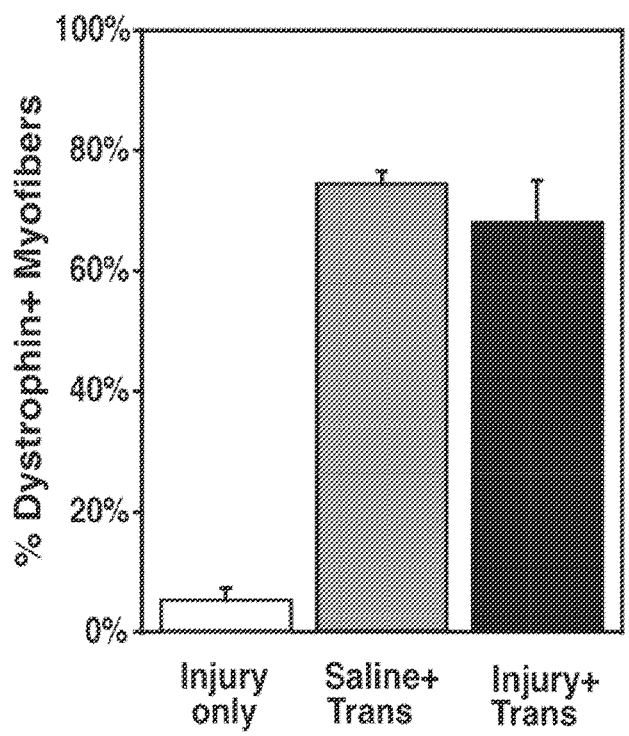
FIG. 12B represents an exemplary histogram illustrating the number of dystrophin expressing myofibers in the transplanted mdx mouse compared to control.

Example 3 illustrates that muscular dystrophy in the TA muscle of the mdx mouse, which has a mutation in the dystrophin gene and is a model for human Duchenne Muscular Dystrophy, can be treated using the method disclosed herein. This is a proof of principal for the use to reduce the onset of muscle damage due to a muscular dystrophy, to treat muscular dystrophy or cure muscular dystrophy. FIG. 12A illustrates that transplantation of 3 myofibers into the TA muscle of the mdx mouse causes a mass increase when the muscle is injured. FIG. 12B illustrates that transplantation of donor myofibers restores dystrophin expression in mdx TA muscle and cures the TA muscle of muscular dystrophy. Sections from the TA muscle illustrate improved muscle histology and a lack of fibrosis and fatty tissue commonly seen in mdx muscle (not shown).

Figure 13:
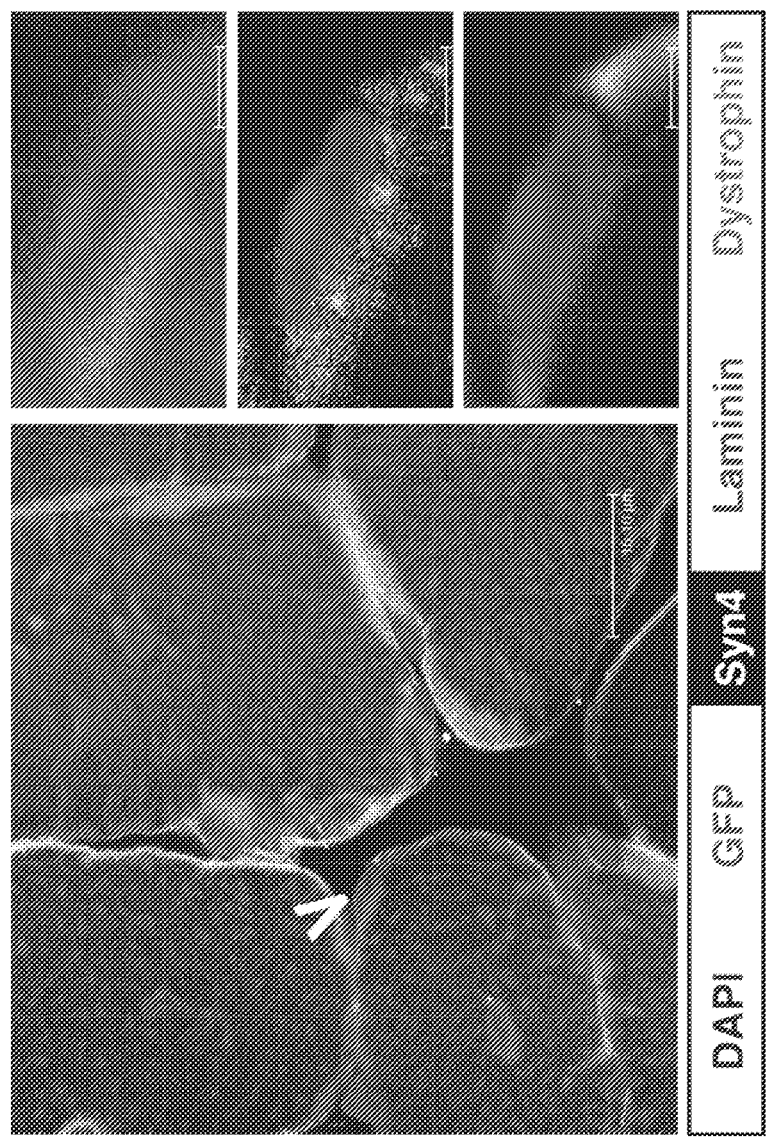
FIG. 13 represents an exemplary digital image illustrating engraftment of donor cells into mdx myofibers and a donor satellite cell in host mdx muscle.

FIG. 13 illustrates donor satellite cells occupying mdx host muscle tissue in myofibers that express dystrophin. The host satellite cell will be able to provide additional dystrophin to the mdx mouse when activated. In addition, this figure illustrates that a single injection into the mdx TA muscle provides long-lasting dystrophin expression through the engraftment of donor satellite cells into the diseased host tissue.

Example 5

The following example illustrates that FGF delivered by muscle tissue transplantation of defective cells increases muscle mass.

In this example the procedure for Example 1 was used to isolate and transplant cells from a mouse lacking the FGF receptor 4 (fgfr4$^{-/-}$) gene. Muscle stem cells from the fgfr4$^{-/-}$ mouse are defective and cannot engraft into a normal host. In the absence of cell engraftment, addition of FGF to fgfr4$^{-/-}$ myofibers and transplantation increases myofiber number similar to transplantation of normal myofibers (data not shown). Delivery of FGF on a myofiber environment promotes muscle mass increases in the absence of cell engraftment. This example shows that muscle mass can be increased in the absence of cell delivery using the myofiber as a carrier of FGF or other growth factors providing a native environment for growth factor delivery.

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

All documents, or portions of documents, cited in this application, including but not limited to patents, patent applications, articles, books, and treatises, are hereby expressly incorporated by reference in their entirety.

What is claimed:

1. A composition consisting essentially of:
   an enriched population of satellite stem cells characterized by expressing at least
   Syndecan-4, ABCG2 and Sca1, whereby the satellite stem cells are capable of generating satellite cells; and
   modified fibroblast growth factor (FGF), wherein the modification increases cellular entry of the fibroblast growth factor.

2. The composition of claim 1, wherein the satellite stem cells are present in an amount of 250 cells or more.

3. The composition of claim 1, wherein the modified FGF comprises FGF-penetratin.

4. The composition of claim 1, wherein the modified FGF is full-length FGF, a biologically active fragment thereof, a chimeric protein, fusion protein or a combination thereof.

5. The composition of claim 4, wherein the modified FGF is a chimeric fibroblast growth factor (FGF) protein comprising: (a) fibroblast growth factor biological activity in the absence of heparan sulfate; and, (b) an ability to enter a living cell in the absence of a receptor that binds to FGF.

6. The composition of claim 1, wherein the satellite stem cells are obtained by harvesting the cells front one or more human donors.

7. The composition of claim 1, wherein the satellite stem cells are Pax7 positive.

8. The composition of claim 1, further comprising a media.

9. The composition of claim 8, wherein the composition is incubated in media for 12 hours or less.

10. The composition of claim 8, wherein the media comprises from about 2% serum to about 15% serum.

11. The composition of claim 8, wherein the satellite stem cells are exposed to the media and the time of exposure is for 24 hours or less.

12. The composition of claim 1, further comprising a pharmaceutically acceptable excipient.

13. The composition of claim 1, wherein the enriched population of satellite stem cells are quiescent prior to adding the modified FGF.

14. A kit comprising:
    at least one container; and
    the composition according to claim 1.

15. The kit of claim 14, further comprising at least one additional growth factor.

16. A method for providing one or more of supplement and replenishment for a muscle cell population in a subject in need thereof, comprising:
    obtaining an enriched population of satellite stem cells characterized by expressing at least Syndecan-4, ABCG2 and Sca1, whereby the satellite stem cells are capable of generating satellite cells;
    incubating the enriched population of satellite stem cells with a media for 24 hours or less;
    providing modified fibroblast growth factor (FGF) to the population, wherein the modification increases cellular entry of the FGF; and
    administering the enriched population of satellite stem cells to muscle tissue of the subject.

17. The method of claim 16, wherein the satellite stem cells are from a donor.

18. The method of claim 17, wherein the donor is an allogeneic donor.

19. The method of claim 17, wherein the donor is a xenogeneic donor.

20. The method of claim 16, further comprising injuring myofibers at a site of muscle transplant in the subject or selecting a site of muscle transplant in a subject that is injured and/or undergoing regeneration.

21. The method of claim 20, wherein injuring the muscle tissue comprises exposing the muscle tissue to a $BaCl_2$ composition.

22. The method of claim 16, wherein the subject has one or more of a muscle injury, aging muscle tissue, a muscle disorder or a neurological disorder that causes muscle loss.

23. The method of claim 16, wherein no more than 30 of the satellite stem cells are administered to the subject.

24. The method of claim 16, wherein the satellite stem cells are from the subject.

25. The method of claim 16, wherein incubating the population with a. media comprises incubating the population for 6 hours or less.

26. The method of claim 16, wherein the modified FGF is full-length FGF, a biologically active fragment thereof, a chimeric protein, fusion protein or a combination thereof.

27. The method of claim 16, wherein the satellite stem cells are Pax7 positive.

28. The method of claim 16, wherein the subject is a human.

29. The method of claim 16, wherein administering comprises one or more of administering by intravenous injection, intra-arterial injection, subcutaneous injection, intramuscular injection or combinations thereof.

* * * * *